(12) United States Patent
Schwarz et al.

(10) Patent No.: US 10,568,936 B2
(45) Date of Patent: Feb. 25, 2020

(54) PHARMACEUTICAL COMPOSITION FOR TRANSMUCOSAL DELIVERY AND METHODS FOR TREATING DIABETES IN A SUBJECT IN NEED THEREOF

(71) Applicant: Eastgate Pharmaceuticals Inc., Toronto (CA)

(72) Inventors: Joseph Schwarz, Toronto (CA); Michael Weisspapir, Toronto (CA)

(73) Assignee: EASTGATE PHARMACEUTICALS INC., Toronto (CA)

( * ) Notice: Subject to any disclaimer, the term of this patent is extended or adjusted under 35 U.S.C. 154(b) by 0 days.

(21) Appl. No.: 14/637,570

(22) Filed: Mar. 4, 2015

(65) Prior Publication Data

US 2015/0250856 A1    Sep. 10, 2015

Related U.S. Application Data

(60) Provisional application No. 61/947,678, filed on Mar. 4, 2014, provisional application No. 61/947,698, filed on Mar. 4, 2014.

(51) Int. Cl.
*A61K 38/28*   (2006.01)

(52) U.S. Cl.
CPC .................... *A61K 38/28* (2013.01)

(58) Field of Classification Search
CPC ........ A61K 38/28; A61K 47/10; A61K 47/12; A61K 47/14
See application file for complete search history.

(56) References Cited

U.S. PATENT DOCUMENTS

| 5,863,555 | A | 1/1999 | Heiber et al. |
| 6,432,383 | B1 | 8/2002 | Modi |
| 6,495,120 | B2 | 12/2002 | McCoy et al. |
| 2004/0063794 | A1 | 4/2004 | Schwarz et al. |
| 2009/0274758 | A1 | 11/2009 | Pinhasi et al. |

FOREIGN PATENT DOCUMENTS

| CA | 2578709 A1 | 1/2006 |
| EP | 2243490 A1 | 10/2010 |
| WO | 2010/118516 A1 | 10/2010 |
| WO | 2014/127459 A1 | 8/2014 |
| WO | 2015/132660 A1 | 9/2015 |

OTHER PUBLICATIONS

Written Opinion and the International Search Report for PCT/IB2015/000390 dated Jul. 21, 2015.
Jain et al.; "Non-Invasive Systemic Delivery of Protein(s) and Peptide(s);" Pharmagene; accepted on Jun. 10, 2013; vol. 1; issue 3, pp. 73-84.
Rekha et al.; "Oral Delivery of Therapeutic Protein/Peptide for Diabetes—Future Perspectives," International Journal of Pharmaceutics; 2013; 440; pp. 48-62.
Madhav et al.; "Recent Trends in Oral Transmucosal Drug Delivery Systems: An Emphasis on the Soft Palatal Route;" Expert Opinion on Drug Delivery; 2012; 9(6); pp. 629-647.
Shojaei et al.; "Systemic Drug Delivery via the Buccal Mucosal Route;" Pharmaceutical Technology; Jun. 2001; pp. 70-81.
Extended European Search Report received in EP 15759080.3 and dated Jul. 38, 2017.

*Primary Examiner* — Gyan Chandra
(74) *Attorney, Agent, or Firm* — Mayer Brown LLP

(57) ABSTRACT

The present disclosure relates to pharmaceutical compositions of solid dosage form for intraoral administration that provides effective delivery of insulin and insulin analogs via the transmucosal route. Also provided are methods for treating pre-diabetes, diabetes and metabolic syndrome in a subject in need thereof.

31 Claims, 11 Drawing Sheets

PHARMACEUTICAL COMPOSITION FOR TRANSMUCOSAL DELIVERY AND METHODS FOR TREATING DIABETES IN A SUBJECT IN NEED THEREOF

CROSS REFERENCE TO RELATED APPLICATIONS

This application claims benefit of U.S. Provisional Patent Application No. 61/947,678 filed on Mar. 4, 2014 and U.S. Provisional Patent Application No. 61/947,698 filed on Mar. 4, 2014; which are incorporated herein by reference in their entirety to the full extent permitted by law.

FIELD

The present disclosure relates to pharmaceutical compositions of solid dosage form for intraoral administration that provides effective delivery of insulin and insulin analogs via the transmucosal route. Also provided are methods for treating pre-diabetes, diabetes and metabolic syndrome in a subject in need thereof.

BACKGROUND

Many drugs cannot be orally administered because the drug will either degrade or will not be orally bioavailable. For example, many drugs undergo acid catalyzed hydrolysis in the stomach, degradation in the gastrointestinal tract, or suffer from first-pass liver effect. Particularly, polypeptide and protein drugs are degraded in the gastrointestinal tract as the gastrointestinal tract protectively digests foreign peptides to deliver amino acid building blocks. There is, therefore, a need for formulations that allow oral administration of drugs that are subject to degradation in the gastrointestinal tract, first-pass liver effect and/or lack permeability in the gastrointestinal tract.

The oral mucosa has been identified as an ideal target to systemically deliver drugs. Permeation through the oral mucosa avoids gastrointestinal degradation and first-pass hepatic effect. Further, permeation through the oral mucosa preempts problems associated with poor gastrointestinal permeation. Thus, a formulation that transports a therapeutically effective agents across the oral mucosa is needed.

Transmucosal permeation occurs through two main pathways—intracellular and intercellular. Intracellular permeation occurs when substances are transferred across the epithelial cell membrane and into the cell prior to systemic delivery. Passive or active transport can drive intracellular permeation. Intercellular permeation occurs when substances diffuse through intercellular lipids. There are two routes associated with the intercellular pathway. The hydrophilic route travels the narrow aqueous regions adjacent to the polar head groups of the membrane lipids. The hydrophobic route travels through the epithelial cell's lipid bilayer.

Diabetes, also referred to as diabetes mellitus, is a metabolic disease that causes high blood glucose level. When blood glucose level rises in a healthy patient, the pancreas converts proinsulin, which is a prohormone precursor to insulin, to another protein called C-peptide and insulin. Insulin promotes the absorption of glucose from the blood. The high blood glucose level is due to either failure to produce enough insulin or to the development of insulin resistance. Failure to produce enough insulin results in diabetes Type I (juvenile diabetes). Type 2 diabetes results from insulin resistance. A third type of diabetes is gestational diabetes which occurs when a pregnant women, without a previous history of diabetes, develops a high blood glucose level. Side effects of this high blood sugar level include frequent urination, increased thirst and increased hunger. If not treated, the high glucose level may cause more serious complications, e.g. hyperglycemia, diabetic ketoacidosis, nonketotic hyperosmolar coma, heart disease, stroke, kidney disease, and nerve damage. Type 1 diabetes is typically treated with insulin or synthetic insulin analogs. Type 2 diabetes may require insulin if other medications fail. With exception to a recently approved pulmonary release formulation, patients requiring insulin must parenterally administer insulin.

Non-parenteral dosage forms for biologically active peptides, especially insulin, are of big demand. Among different non-injectable delivery methods of insulin, oral administration of this peptide is one of the most promising delivery methods. The pharmaceutical industry has searched for an oral insulin for more than 90 years. Indeed, the first oral insulin experiments in man occurred in 1922. Since then, numerous patents and publications have advertised an oral method of insulin administration and numerous formulations have entered clinical trials. Despite tremendous efforts, very few products are marketed or have reached late stages of development. Due to peptide nature, insulin molecule in oral formulations must be protected from enzymatic degradation in the gastro-intestinal tract. It requires incorporation of protease inhibitors into formulations, and extended use of such inhibitors may cause serious side effects.

Inhalable insulin formulation (e.g., Exubera®) was withdrawn from the market due to insufficient uptake in the market. Oral sprays (e.g., Ora-Lyn™) require multiple administrations and an expensive and complex delivery device. Intranasal peptide delivery has limitations due to often irritation and sensitization. (Heinemann et al., "*Oral Insulin and Buccal Insulin: A Critical Reappraisal,*" *J. Diabetes Sci. Technol.*, 2009, 3(3): 568-584; Soares, S., "*Novel Non-Invasive Methods of Insulin Delivery,*" *Expert Opin. Drug Deliv.*, 2012, 9(12): 1539-1558).

Intraoral route of delivery of different peptides attracted tremendous attention in the last decades. Oral mucosa has good potential as an excellent place for enhanced delivery of various drugs, including peptides.

Buccal and sublingual mucosa is relatively easy penetrable for small, especially hydrophobic, molecules (below 500 Dalton). In order to overcome penetration resistance of mucosa to large hydrophilic peptide molecules, various approaches have been exploited. These approaches include the use of penetration enhancers such as polar solvents—liquid PEGs, Propylene glycol, DMSO, N-Mehtylpyrrolidone; lipid disturbants—Azone®, Decylmethylsulfoxide; non-ionic surfactants—polysorbates, poloxamers, alkyl glucosides and other sugar esters; anionic surfactants—sodium lauryl sulfate (SLS), salts of fatty acid; phospholipids—lecithin, phosphatidylcholines, other phospholipids; bile acids—sodium cholate, desoxycholate, taurocholate and analogs; high concentrations of terpenes—menthol, borneol, eucalyptol; chelators—EDTA, citric acid, etc.; lipids and esters—mono-, di- and triglycerides, glycol esters, various cyclodextrines and other compounds. (Kinesh et al., "Novel *Approaches for Oral Delivery of Insulin and Current Status of Oral Insulin Products,*" International Journal *of Pharmaceutical Sciences and Nanotechnology,* 2010, 3(3): 1057-1064). Furthermore, WO 2012/104834 teaches a buccal bioadhesive polymeric film loaded with insulin and penetration enhancers; WO 2011/086093 describes liquid self-nanoemulsifying systems for oral delivery of acylated derivatives of insulin based on combination of polar solvent and non-ionic surfactants, and WO 2005/089722 describes the sublingual composition of insulin combined with chelators such as EDTA and citric acid in order to prevent insulin's aggregation into hexamers.

The influence of various penetration enhancers on the membrane fluidity and insulin delivery "in vitro" and "in vivo" was investigated by Cui et al. (Cui et al., "*Sublingual delivery of insulin: effects of enhancers on the mucosal lipid fluidity and protein conformation, transport, and in vivo hypoglycemic activity,*" Biol. Pharm. Bull., 2005, 28(12): 2279-2288). The enhancing effects may be due to one or multiple factors such as increasing the mucosal lipid fluidity, directly loosing the tight junction of epithelia, and other parameters. Cui et al. evaluated effects of enhancers on the mucosal lipid fluidity and protein conformation, transport, and hypoglycemic activity in normal rats. The formulations contained high levels of the enhancers—5 to 10% of the liquid composition. For evaluating transport of insulin, human immortalized oral epithelial cell monolayer was used. The penetration enhancers that were used include hydroxylpropyl-beta-cyclodextrin (HP-beta-CD), chitosan, polyethylene-polypropylene glycol, polyoxyethylene lauryl ether, polysorbate 80, egg lecithin and oleic acid.

Aungst et al. tested efficacy of various penetration adjuvants, including non-ionic surfactants, bile salts, fatty acids, enzymes, polar solvents and their combinations on buccal insulin delivery in high concentration. (Aungst et al., "*Comparison of the effects of various transmucosal absorption promoters on buccal insulin delivery,*" International Journal of Pharmaceutics, 1989, 53: 227-235). It was found that most of such adjuvants are effective only when used at high concentrations (5-10%).

In order to improve bioavailability of transmucosally delivered peptides, the peptides can be incorporated into nanoparticles, micro- and nanoemulsions, micellar solutions or self-emulsifying compositions. Various solid, semi-solid and liquid dosage forms as well as pressurized sprays, buccal films and patches were proposed for intraoral administering of peptides. (Xu et al., "*Hypoglycaemic Effect of a Novel Insulin Buccal Formulation nn Rabbits,*" Pharmacological Research, 2002, 46(5):459-467; Elsayed et al., "*Formulation and Characterization of an Oily-Based System for Oral Delivery of Insulin,*" Eur. J. Pharm. Biopharm., 2009, 73: 269-279; Sarmento et al., "*Oral Insulin Delivery by Means of Solid Lipid Nanoparticles,*" Inter. J. Nanomed., 2007, 2(4): 743-749).

For example, U.S. Pat. No. 6,290,987 discloses a mixed liposomal formulation containing alkylsulfate salts delivered intra-orally as a spray. U.S. Pat. No. 6,350,458 denotes use of mixed micelles for transbuccal delivery of insulin. Proposed oral spray compositions contain high concentration of alkylsulfates, such as sodium lauryl sulfate, possessing high irritation potential for oral mucosa.

Furthermore, U.S. Pat. No. 6,635,617 teaches pulmonary delivery of insulin in combination with menthol, using bronchodilatory properties of this terpene. U.S. Pat. No. 7,112,561 describes use of macrocyclic penetration enhancers in nasal formulations for insulin emulsions in acidic conditions. Moreover, U.S. Pat. No. 4,579,730 describes cholate complexes of insulin with protease inhibitors for oral delivery.

The use of various complexes and biodegradable nanoparticles with sodium deoxycholate as ion-pair reagent for enhancement of insulin delivery has also been described. (Sun et al., "*Hydrophobic Ion Pairing of an Insulin—Sodium Deoxycholate Complex for Oral Delivery of Insulin,*" Int. J. Nanomed., 2011, 6:3049-3056).

Various penetration enhancers were proposed for increasing of transmucosal transportation of peptides and proteins: polar solvents (PG, DMSO); terpenes (menthol, borneol); surfactants (Brij, SLS). For example, U.S. Patent Publication No. 2004/0258623 describes oral spray containing insulin, lecithin, polar solvent and borneol as penetration enhancers. U.S. Patent Publication No. 2009/0274758 describes solid composition for intraoral delivery of different types of biologically active molecules, including insulin, using hydrophilic polymeric matrixes or liquid formulations, containing liposomes or pro-liposomal combinations together with menthol as a penetration enhancer and sodium lauryl sulfate (SLS) and other anionic surfactants. Due to proposed very high concentrations of SLS and menthol, such formulations should possess serious local irritation potential. Shojaei et al. teach an effective transbuccal penetration enhancer. (Shojaei et al., "*Transbuccal Permeation of a Nucleoside Analog, Dideoxycytidine: Effects of Menthol as a Permeation Enhancer,*" Int. J. Pharm., 1999, 192: 139-146).

Significant improvement of transdermal or transmucosal penetration for polar compounds can be achieved by applying high concentrations of such enhancers. In most cases it associated with serious local irritation, especially for intranasal route of administration. Tissue damage and delipidization, loss of taste and odor sense may be caused by administration of formulations with high concentration of penetration enhancers.

Various microemulsions and nanoemulsions, especially in self-emulsifying pre-concentrates, were widely investigated as delivery systems for oral delivery of peptides, including insulin. Spontaneously formed colloidal dispersions are absorbed in gastro-intestinal tract and could increase efficacy of drug absorption in some cases. As described in WO 2011/086093, combination of insulin and polar organic solvent with low content of lipids and elevated concentration of surfactants with high HLB, administered into duodenum or distant parts of intestine, improved insulin delivery via gastro-intestinal tract.

Transmucosal delivery improvement can be achieved with various eutectic mixtures. An eutectic mixture is a mixture of two or more substances that melts at a temperature lower than the melting point of any single component or any other mixture of them. A simple eutectic mixture consists of two compounds that are completely miscible in liquid state but only to a very limited extent in a solid state. (*Remington: The Science And Practice of Pharmacy*, 2000, 20$^{th}$ edition, Lippincott Williams & Wilkins, Philadelphia, pp. 177). Formation of eutectic mixtures can not be predicted based on molecular structure and composition of components. The properties of such mixtures can be determined only experimentally.

The well known eutectic mixtures used in pharmaceutical development are menthol and camphor mixtures having high solubilizing properties for non-steroidal anti-inflammatory compounds (U.S. Pat. No. 7,138,394). Phenol or menthol combinations with various compounds, cause incompatibility problems in pharmaceutical formulations; e.g., in mixtures with antipyrine, salycilates, acetaminophen and alkaloids. (*Remington: The Science And Practice of Pharmacy*, 2000, 20$^{th}$ edition, Lippincott Williams & Wilkins, Philadelphia, pp. 1045).

The eutectic mixture of solid crystalline bases of Lidocaine and Prilocaine is liquid at room temperature and had been successively used for preparation of topical local anesthetic cream with enhanced efficacy. (EMLA® Product Information, available at: www.medicines.org.au/files/appemlac.pdf).

Menthol was found to form eutectic mixtures with testosterone, cholesteryl oleate, and ceramides. Eutectic mixture of menthol (m.p. ~42° C.) and testosterone (m.p. ~155° C.) is solid at body temperature (melting point ~40° C.) but shows increased transdermal penetration of the drug. The decrease in melting temperature resulted in an increase in the solubility of testosterone in an aqueous ethanol vehicle by 2.8-fold, which caused a corresponding 2.8-fold increase in the flux of testosterone. A further increase in skin flux, to eight times the base line, could be attributed to the effect of high concentration of menthol on the skin barrier properties. (Kaplun-Frischoff, et al., "*Testosterone Skin Permeation Enhancement by Menthol Through Formation of Eutectic with Drug and Interaction with Skin Lipids,*" J. Pharm. Sci., 1997, 86(12):1394-1399).

U.S. Patent Publication No. 2007/024261 describes several liquid eutectic compositions, suitable for oral administration of encapsulated drug formulation dosage. U.S. Pat. No. 8,790,723 describes methods of solid dosage forms preparation of coenzyme Q10 with enhanced bioavailability.

Goldberg found that eutectic mixtures may provide a unique approach for increasing dissolution rates. (Goldberg et al., "*Increasing Dissolution Rates and Gastrointestinal Absorption of Drugs Via Solid Solutions and Eutectic Mixtures I. Theoretical Considerations and Discussion of the Literature,*" J. Pharm. Sci., 1965, 54(8):1145-1148; Goldberg et al., "*Increasing Dissolution Rates and Gastrointestinal Absorption of Drugs Via Solid Solutions and Eutectic Mixtures II: Experimental Evaluation of a Eutectic Mixture: Urea-Acetaminophen System,*" J. Pharm. Sci., 1966, 55(5):482-487). Eutectic mixtures of fatty acids, liquid at body temperatures, are described by Zhang et al. (Zhang et al., "*Thermal studies on the solid-liquid phase transition in binary systems of fatty acids,*" Thermochimica Acta., 2001, 369: 157-160).

Bile acids and salts thereof are widely used as penetration enhancers for peptides and proteins. Das et al. developed optimized buccal insulin-loaded Pluronic F-127 gels. Bioadhesive gels with insulin, surfactants and bile acid derivatives for buccal and sublingual delivery were prepared. [N. Das et al., "*Development and in Vitro Evaluation of Insulin-Loaded Buccal Pluronic F-127 Gels,*" Pharmaceutical Development and Technology, 2010, 15(2):192-208). Bioadhesive sublingual tablets containing chitosan and various biologically active compounds, including insulin and sildenafil were described in WO 2010/118516.

Nevertheless, despite numerous attempts, the need to develop a non-invasive delivery system for insulin is still unmet and compels development of stable convenient intraoral dosage forms of insulin. Accordingly, there is a need for a therapeutically effective oral insulin formulation. The present teachings provides formulations that permeate drugs through the oral mucosa.

SUMMARY

The present disclosure relates to intraoral solid pharmaceutical compositions for sublingual or buccal administration, containing a biologically active peptide, such as insulin or insulin analogs. The object of the disclosure is to provide safe and convenient method for transmucosal delivery of insulin, providing fast onset of glucose lowering action.

In one embodiment, the disclosure provides effective transmucosal delivery of biologically active polypeptide, such as insulin, by sublingual administration of solid dosage form, comprising the protein and eutectic mixture of at least two hydrophobic components.

In another embodiment, the eutectic mixture is liquid at body temperature or has melting point noticeably lower than melting point of any of the individual components.

In yet another embodiment, the eutectic mixture is incorporated into solid dosage form, such as compressed tablet, lozenge or another orally dissolving form.

According to embodiment of the disclosure, the eutectic mixture of hydrophobic components forms the oil phase of the oil-in-water emulsion by itself or the eutectic mixture is incorporated into the hydrophobic (e.g., lipid) phase of this emulsion.

In another embodiment, the eutectic mixture may be dissolved in a hydrophobic phase of the emulsion, and such hydrophobic phase may comprise either components of the eutectic mixture or other physiologically acceptable compounds, such as edible oils, mono-, di- and triglycerides, essential oils, tocopherols, tocotrienols, aliphatic and aromatic esters of fatty acids and organic acids.

In one embodiment, the emulsion is formed spontaneously after the dosage form is contacted with saliva or a wet mucosal surface.

In another embodiment, the droplet size of the formed emulsion is smaller than 1 micrometer, usually the droplets size is between 2-200 nm.

In yet another embodiment, the compounds forming the eutectic mixture are safe and physiologically acceptable. The compounds forming the eutectic mixture are selected from groups of fatty acids, cyclic alcohols, tocopherol derivatives, phospholipids, sterols and phenolic compounds. Such eutectic mixture can be incorporated into hydrophobic composition forming oil droplets of the emulsion, as a part, or build such droplets of the emulsion by itself, being hydrophobic in nature.

Another embodiment of the disclosure relates to incorporation of hydrophobic eutectic mixture components in relatively low concentrations into the core of spontaneously formed nanocolloids (nanoemulsions, mixed micelles). This may noticeably improve transmucosal penetration of polypeptides, such as insulin and insulin analogs. It was surprisingly found that incorporation of eutectic mixture into the hydrophobic core of emulsion droplets, simultaneously formed after dissolution of sublingual or buccal intraoral dosage form noticeably enhances transmucosal penetration of biologically active protein or peptide, such as insulin or insulin analogs. This may be associated with liquefying and improved fluidity of lipid membranes of mucosal liner cells. Interaction of eutectic mixture components with cellular membrane results in decrease of melting point of structural membrane lipids. The process can be caused by combination of high infiltration rate of tiny oil droplets and decrease of melting points of cell membrane lipids by interacting these lipids with components of the eutectic mixture. Higher fluidity of the membranes increases transmucosal penetration of the active components, associated with hydrophobic droplets. Incorporation of hydrophobic eutectic mixtures into self-emulsifying formulation in accordance with the present disclosure improves insulin penetration in higher extent than similar emulsions without eutectic components.

In yet another embodiment, the insulin molecule is associated with oil droplets of the formed emulsion with the help of a hydrophobic counter ion. The use of counter-ions associated with a polypeptide molecule increases both the hydrophobization of the polypeptide molecule and the association with hydrophobic core part of nanoemulsion containing eutectic mixtures. Moreover, the counter-ion molecule, such as organic acid, can be a component of eutectic mixture. Transmucosal delivery improvement was achieved with various eutectic mixtures, e.g., combination of menthol and vitamin E succinate, menthol and hydrogenated or purified lecithins, thymol and vitamin E succinate, fatty acid mixtures such as combination of lauric and stearic acids or lauric and palmitic acids, cholesterol and oleic acid. Various tablet formulations were obtained with diacylphosphatidyl-glycerol derivatives, cholates, deoxycholates, cholesteryl sulfate, used as hydrophobic counter-ions.

In one embodiment, the dosage form for intraoral transmucosal delivery of insulin and other peptides is a compressed tablet. Additionally the tablet can comprise non-ionic surfactants, fillers, such as pharmaceutical grade polyols or sugars (e.g., sucrose, sorbitol, mannitol, erythritol), binders (PVP, cellulose esters, polyethylene glycols), disintegrants (cross-carmellose, cross-povidone), preservatives (e.g., parabens, sorbic acid, benzoic acid and pharmaceutically acceptable salts thereof), lubricants, glidants, flavors, antioxidants, etc. These components are incorporated into the tablet matrix, prepared by granulation, blending and compression. According to the disclosure, the compressed sublingual tablet contains insulin in combination with surfactant, eutectic mixture, counter-ion and hydrophobic phase, spontaneously forming nanoemulsion on contact with saliva.

According to one embodiment, the hardness of the compressed tablet should be in range of 2-16 kP or higher.

By another aspect of the invention, the dosage form for sublingual administration of insulin and insulin analogs should dissolve in the mouth in 3-30 minutes.

Tablet matrix granulate, containing insulin and other excipients that suitable for compression, could be prepared by wet granulation, compaction, trituration or dry blending. Tablets were compressed into round, oval or other required shape tablets using appropriate tablet press.

In a preferred embodiment of the disclosure a solid dosage form (compressed tablet) for intraoral administration comprises 0.5-10 mg of insulin or insulin analog, embedded into composition containing hydrophobic eutectic mixture which melts below 37° C., physiologically acceptable oil phase, a counter-ion, a non-ionic surfactant, an emulsifier, a filler, a glidant, a flavoring agent, a lubricant, an antimicrobial preservative, and insulin or insulin analog peptide is at least partially associated with an oil droplets of the "in situ" forming emulsion which is released from this dosage form upon contact with saliva.

Other embodiments, objects, features, and advantages will be set forth in the detailed description of the embodiments that follow and, in part, will be apparent from the description or may be learned by practice of the claimed invention. These objects and advantages will be realized and attained by the compositions and methods described and claimed herein. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled. Other features and iterations of the disclosure are described in more detail below.

BRIEF DESCRIPTION OF THE DRAWINGS

FIG. 8A is a graphic presentation of the maximal glucose drop compared with initial level and FIG. 8B presents maximal drop of glucose level after subtraction of baseline value of glucose drop (13% of initial).

DETAILED DESCRIPTION

Figure 1:
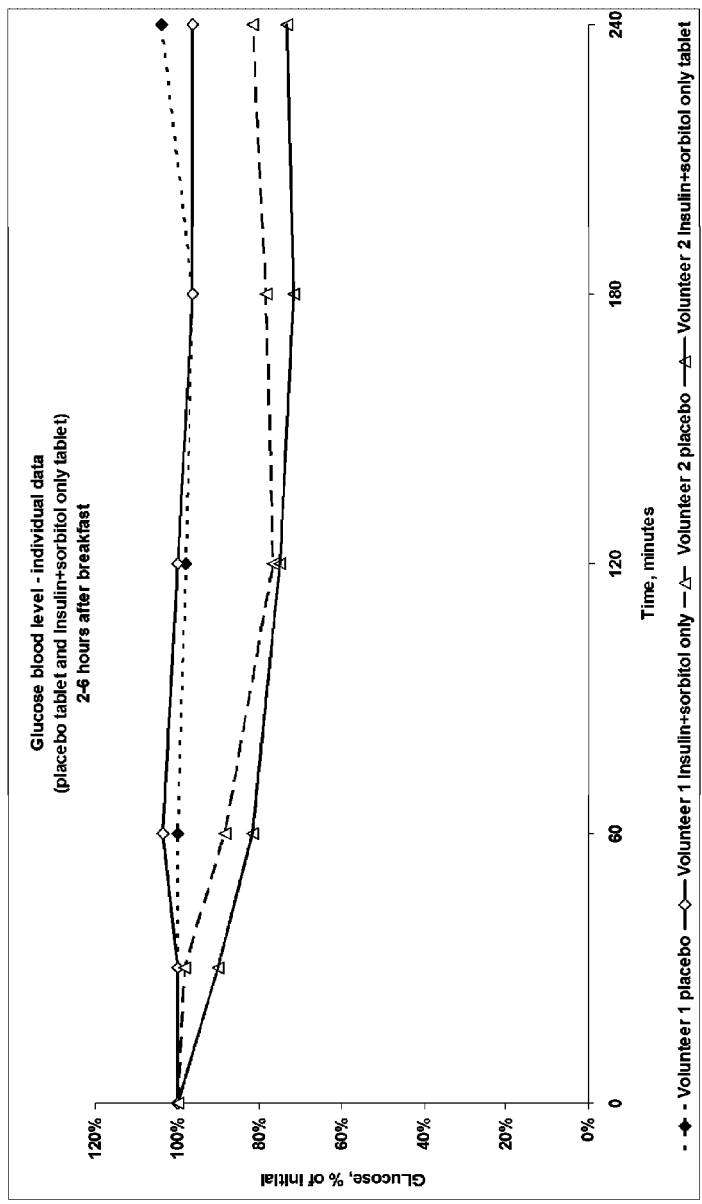
FIG. 1 is a graphic presentation of glucose level changes over the time after sublingual administration of the placebo tablet (dashed lines) and the tablet, containing only insulin (50 units) in sorbitol matrix (solid lines).
Figure 2:
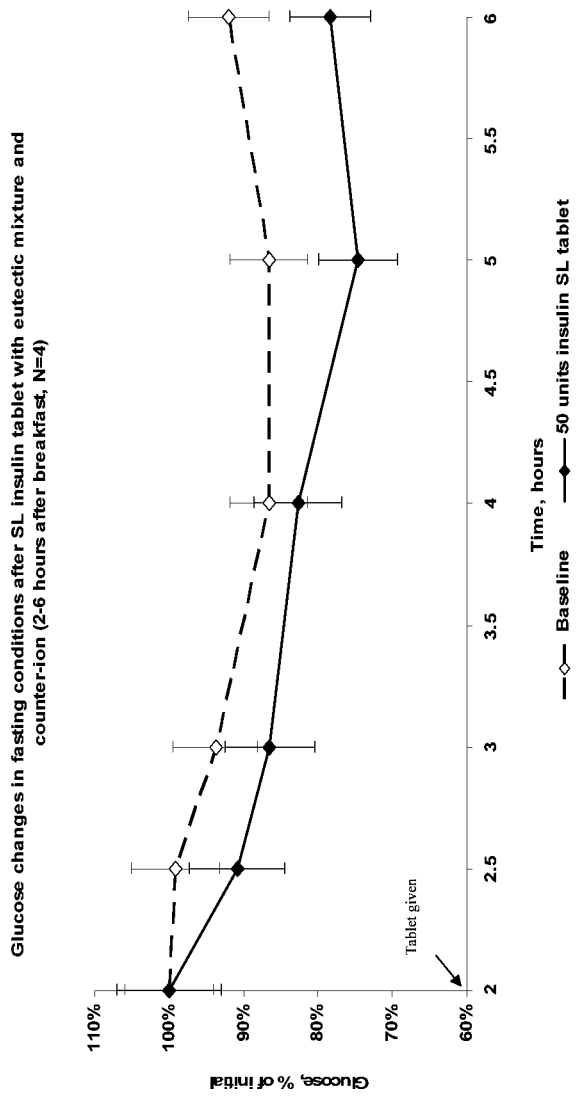
FIG. 2 is a graphic presentation of average glucose level relative changes over the time after sublingual administration of the placebo tablet (dashed line) and insulin (50 units) tablet in a matrix, containing a self-emulsifying eutectic mixture (menthol based), counter-ion, bile salt and flavor (solid line).
Figure 3:
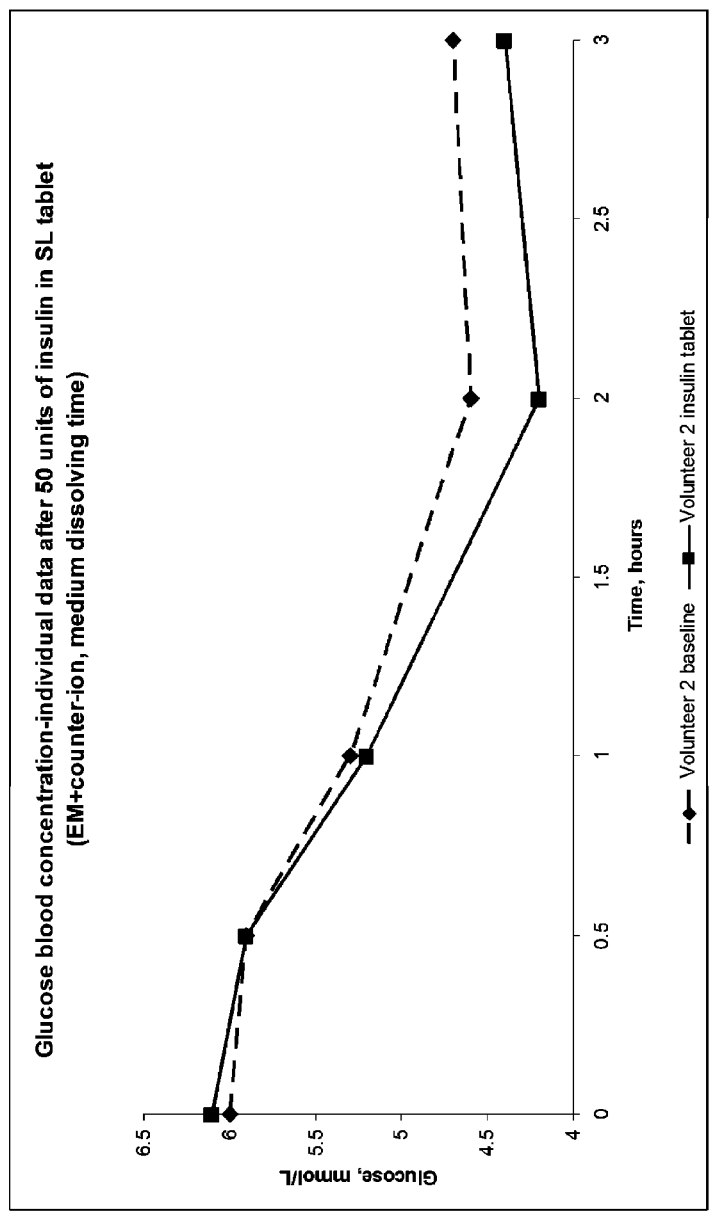
FIG. 3 is a graphic presentation of individual glucose level changes over the time after sublingual administration an insulin (50 units) tablet in a matrix, containing a self-emulsifying eutectic mixture (menthol based) and counter-ion (solid line) with medium dissolving time, compared with individual glucose level baseline (dashed line).
Figure 4:
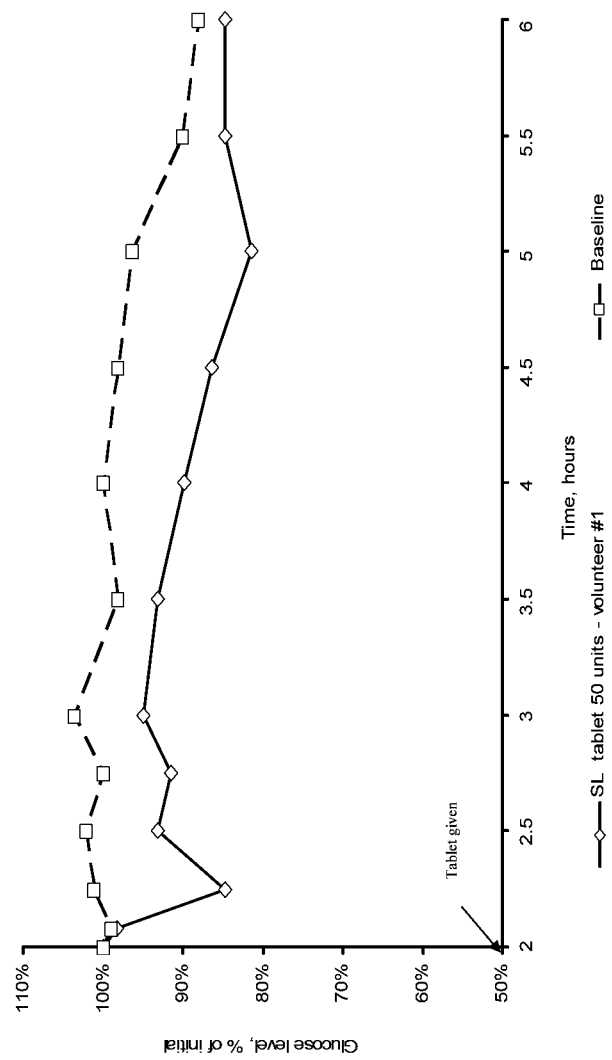
FIG. 4 is a graphic presentation of relative individual glucose level changes over the time after sublingual administration insulin (50 units) tablet in a matrix, containing a self-emulsifying eutectic mixture (menthol based), counter-ion, bile salt and flavor (solid line), compared with relative individual glucose level baseline (dashed line).

While the present disclosure is capable of being embodied in various forms, the description below of several embodiments is made with the understanding that the present disclosure is to be considered as an exemplification of the claimed subject matter, and is not intended to limit the appended claims to the specific embodiments illustrated and/or described, and should not be construed to limit the scope or breadth of the present disclosure. The headings used throughout this disclosure are provided for convenience only and are not to be construed to limit the claims in any way. Embodiments illustrated under any heading may be combined with embodiments illustrated under any other heading.

Solid dosage forms for systemic transmucosal delivery of biologically active proteins and peptides, preferably insulin, with fast onset of action, are described. The formulations contain peptide, such as insulin, insulin analogs, or precursors, in combination with surfactant and eutectic mixture of hydrophobic compounds, and optionally additional physiologically acceptable excipients. A eutectic mixture serves as efficient penetration promoter for fast permeation of large protein molecules. Incorporation of a eutectic mixture into a self-emulsifying delivery system, forming emulsions "in situ" upon a tablet contact with saliva or wet mucosal surface, improves transport of the eutectic components to membranes of mucosal cells. The incorporation of a eutectic mixture into lipid bilayers of the cell membranes increases membrane fluidity and flexibility, enhancing transportation of the peptides through the oral lining. Eutectic components, dissolved in the oil droplets of nanoemulsions, may reach mucosal tissues faster than simple solutions of penetration enhancers since precipitation of the insoluble components is avoided.

After buccal or sublingual administration insulin or other biologically active peptide, associated with tiny oil droplets of the formed emulsion, penetrates through mucosal tissues and enters blood circulation avoiding enzymatic digesting. In the preferred embodiment of the invention an insulin containing formulation is a compressed tablet, administered sublingually to control glucose level.

As it was surprisingly found, that the best glucose-lowering efficacy was achieved when solid dosage forms match the following requirements:

The dosage form (compressed tablet) releases oil-in-water emulsion after contact with saliva.

The tablet contains physiologically acceptable eutectic mixture, which is liquid at body temperature (with melting point below 37° C.). Eutectic mixture can contain two, three or more components (combination of menthol, fatty acids, tocopheryl esters, phospholipids, etc.).

The eutectic mixture incorporated into hydrophobic core of the formed emulsion or this core is a eutectic mixture itself The prepared self-emulsifying composition contains at list one non-ionic surfactant in relatively low concentration.

Association of peptide (e.g., insulin or insulin analogs) with oil droplets of the emulsion could be enhanced with the use of physiologically acceptable counter-ions, usually negatively charged (cholates, glycyrrhizates, phosphoglycerides, tocopherol succinate, oleate, etc.).

The tablet contains penetration enhancers (menthol, cholates) in relatively low concentration to avoid damage of mucosal tissues.

Figure 5:
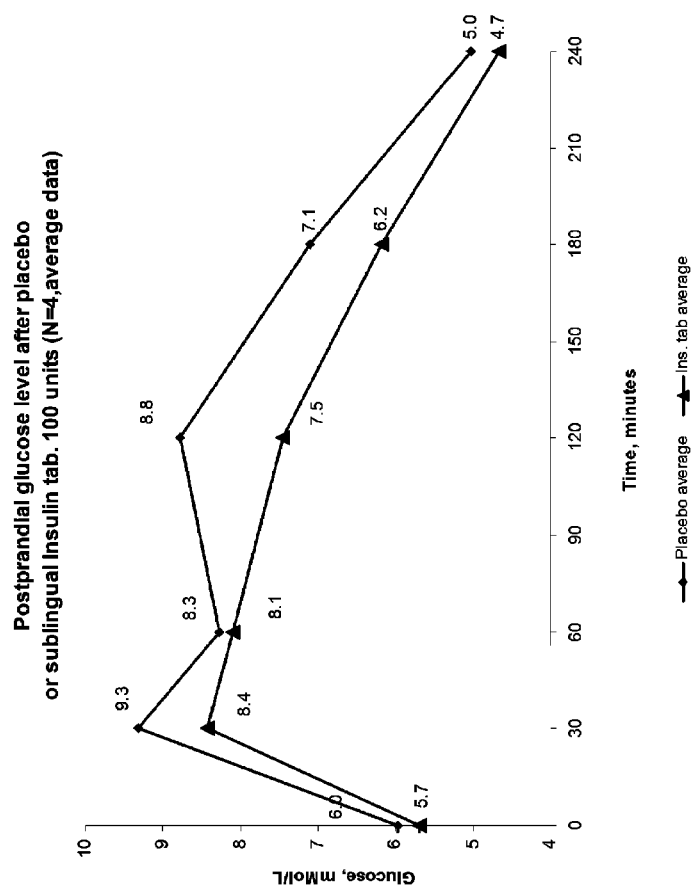
FIG. 5 is a graphic presentation of postprandial glucose level changes over the time after sublingual administration insulin (100 units) in a matrix, containing a self-emulsifying eutectic mixture (menthol based), counter-ion, bile salt and flavor (triangles), compared with glucose level in placebo treated group (diamonds). Sublingual insulin was delivered 30 minutes before standardized breakfast meals (710 kCal) and visibly decreased postprandial peak glucose.

The composition may be beneficial for pre-diabetic and newly diagnosed diabetic patients, especially for Diabetes Mellitus (Type 2). Administration of sublingual insulin tablet before meals prevents excessive elevation of sugar level in blood caused by not adequate control of glucose regulation in patient's body. (FIG. 5)

The transportation of a polar hydrophilic polypeptide or protein molecule through mucosal membrane can be alleviated by decrease of the resistance of mucosal tissues to drug diffusion. The oral mucosa can be subdivided according to the major regions in the oral cavity, a so-called non-keratinized area consisting of the floor of the mouth (sublingual), the buccal mucosa (cheeks), and a keratinized area comprising the gum (gingiva), the palatal mucosa, and the inner side of the lips. The rapid turnover of the epithelial cells relative to the skin is an important feature of the oral cavity that affects drug absorption by continually changing permeability characteristics.

The buccal epithelium is a non-keratinized squamous layer of cells, 500-600 µm in thickness, composed of strata of different cell types with varying maturity. The upper most superficial region is comprised of flattened compact layers of differentiated cells, about 150 µm thick. The buccal epithelium is highly vascularized and the papillary contour of the basal region permits efficient vascularization of the cells. Hydration of the mucous membranes, due to the contact with saliva, may strongly facilitate drug permeation. However, the mucus layer is small relative to other barriers that peptides encounter during their passage through the buccal mucosa.

Oral mucosal tissue contains a large amount of extracellular material, which not only gives the epithelium its elasticity but is also thought to contribute to the permeability barrier. Regional differences in permeability are dependent upon epithelial thickness, the eventual presence of a keratinized epithelium and the organization of intercellular material extruded by membrane-coating granules in the upper layers of the epithelium. Buccal mucosa contains mostly polar lipids such as phospholipids, cholesterol sulfate and glycosylceramides. This may result in fluidity and may create micro domains with specific properties. The non-keratinized regions have higher permeability to water and hydrophilic compounds than keratinized areas. (Veuilleza, et al., "Factors and Strategies for Improving Buccal Absorption of Peptides," Eur. J. Pharm. Biopharm., 2001, 51:93-109).

Two main pathways seem to be associated with peptide transport through membranous tissues: the intracellular (transcellular) pathway where peptides traverse the epithelium across the cells, and the intercellular pathway where peptides diffuse through the intercellular lipids. The transcellular route may involve permeation across the apical cell membrane, the intracellular space and the basolateral membrane either by passive transport (diffusion, pH, partition) or by active transport (facilitated and carrier-mediated diffusion, endocytosis). The transcellular permeability of a peptide is a complex function of various physicochemical properties including size, lipophilicity, hydrogen bond potential, charge and conformation. Small polar molecules penetrate buccal epithelium via the intracellular route. The drug transport via aqueous pores in the cell membranes of the epithelium is also possible for substances of low molar size. The second route, available to substances of a wide range of molecular weight, is an intercellular (paracellular) route. Within the intercellular space, there probably exist at least two pathways, one is essentially a hydrophobic route through the lipidic bilayer, while the second is more hydrophilic and associated with the narrow aqueous regions adjacent to the polar head groups of the lipids. A consequence of these two pathways is that the substances having nearly equal solubility in water and oil, traverse using both routes. Peptides are presumed to permeate through the aqueous pathways, i.e. the paracellular and aqueous pore paths. Paracellular transport occurs between the epithelial cells by passive diffusion across the intercellular junctional complex of the epithelium. It has also known that the oral mucosae contain carrier-mediated (active) transportation systems for small molecules and short peptides. (Veuillez et al., "Factors and Strategies for Improving Buccal Absorption of Peptides," Eur. J. Pharm. Biopharm., 2001, 51(2): 93-109).

According to current paradigm, penetration enhancers improve mucosal peptide absorption by changing mucus rheology, i.e., reducing the viscosity and elasticity of mucus layer, as well as by increasing membrane fluidity and hence facilitating transcellular transport.

Utilization of polar organic molecules (NMP, DMSO, DMA, Azone, terpenes, propylene glycol, etc.) as penetration enhancers associated with irritation of mucosa, local or systemic toxicity and unpleasant taste of many of such compounds. Also due to high solubility in water most of these compounds cannot be incorporated into lipophilic membranes and modify membrane fluidity. Moreover, some surfactants (sodium lauryl sulfate, sodium laurate, acyl glycosides, nonoxynol, Brij, alkaline salts of fatty acids and salicylic acid), used as penetration enhancers, may destruct cell membranes and cause irritation.

Non-surfactants, e.g., terpenes (menthol, borneol), can modify fluidity of mucosal lipids, but for this effect they need to be used in relatively high concentrations, causing irritation and unpleasant taste changes.

Incorporation of insulin into colloidal delivery systems, such as nanoparticles or liposomes, may improve drug transportation, but due to high water solubility of the protein efficacy of drug incorporation remains low. It can be improved by addition of appropriate counter-ions, increasing hydrophobicity of proteins and peptides.

It can be hypothesized that some of penetration enhancers may interact with lipid components after penetration into mucosal layer and forming some kind of eutectic mixtures thus causing increased lipid fluidity and better penetration of targeted components.

It was unexpectedly found that preformed eutectic mixture, incorporated into colloidal delivery system, e.g., emulsion, nanoemulsion or micelles in a relatively low amount, provides fast and effective improvement of penetration of peptides and proteins. The onset of biological effect of peptides occurs faster with formulations containing eutectic mixtures than formulations with high concentrations of penetration enhancers and surfactants only.

I. Definitions

For convenience, before further description of the present teachings, certain terms employed in the specification, examples, and appended claims are collected here. These definitions should be read in light of the remainder of the disclosure and as understood by a person of ordinary skill in the art. Unless defined otherwise, all technical and scientific terms used herein have the same meaning as commonly understood by a person of ordinary skill in the art.

A. General Terms

The use of the terms "a," "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

The phrase "and/or," as used herein, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements).

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein, the phrase "at least one" in reference to a list of one or more elements should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, all transitional phrases such as "comprising," "including," "carrying," "having," "containing," "involving," "holding," "associated," "associated with," and the like are to be understood to be open-ended, i.e. to mean including but not limited to.

The use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

B. Terms Related to Compositions of the Present Disclosure

As used herein, "insulin" includes native insulin, proinsulin, insulin prodrugs, insulin analog, insulin derivatives, recombinant insulin or insulin from any origin, or any acceptable form thereof, which have activity similar to native insulin.

"Buccal mucosa" includes the portion of the oral mucosa that lines the cheeks.

"Oral mucosa" includes the mucus membrane lining the inside of the mouth and consists of stratified squamous epithelium termed oral epithelium.

A "eutectic mixture" refers to a mixture of two or more substances that melt at a temperature lower than the melting point of any of the substances individually or any other mixture of the substances. Not wishing to be held to theory, the eutectic mixture forms a crystal lattice weaker than that of the pure substances or other mixtures, which lowers the amount of energy required to melt the eutectic mixture compared to the pure substances or other mixtures.

As used herein "penetration enhancer" refers to a compound or mixture of compounds that increase the permeation of one or more drugs through epithelial cells. A penetration enhancer increases systemic delivery of one or more drugs.

"Permeate" or "permeation" refers to movement of a substance into or through epithelial cells. Permeation through epithelial cells delivers the substance systemically. Permeation may occur through an intracellular or intercellular pathway by either active or passive transport.

"Sub-lingual mucosa" includes the portion of the oral mucosa located under the tongue.

A "surfactant" refers to an organic compound that contains both a hydrophobic group and a hydrophilic group. The hydrophilic group is often referred to as the head and the hydrophobic group as the tail. A surfactant will adsorb at interfaces between hydrophilic compositions, such as oil, and hydrophilic compositions, such as water, wherein the hydrophilic head will extend into the water and the hydrophobic tail will extend into the oil. As used herein, a "anionic surfactant" is a surfactant that contains an anionic functional group or groups at its hydrophilic head. Non-limiting examples of an anionic function groups are sulfate, sulfonate, phosphate, and carboxylates. As used herein, a "nonionic surfactant" are surfactants that do not contain a charged functional group. Non-limiting examples of nonionic surfactants are fatty alcohols.

C. Terms Related to Methods of Treatment

As used herein, "oral administration" refers to treatment of a disease or disorder by delivery of therapeutically effective agents through the mouth. The agent may permeate through the oral mucosa or anywhere throughout the gastrointestinal tract. Oral administration includes, but is not limited to, solid dosage forms such as tablet, chewable tablet, lozenge, powder, dissolving film, gum, as well as homogenous and heterogeneous liquids, including emulsions.

A "subject" or a "patient" refers to any mammal (e.g., a human), such as a mammal that may be susceptible to a disease or disorder, for example, diabetes. Examples include a human, a non-human primate, a cow, a horse, a pig, a sheep, a goat, a dog, a cat, or a rodent such as a mouse, a rat, a hamster, or a guinea pig. In various embodiments, a subject refers to one that has been or will be the object of treatment, observation, or experiment. For example, a subject can be a subject diagnosed with diabetes or otherwise known to have diabetes or is a subject selected for treatment, observation, or experiment on the basis of a known diabetes in the subject.

As used herein, "treat," "treatment" or "treating" refers to an amelioration of a disease or disorder, or at least one sign or symptom thereof. In another embodiment, "treatment" or "treating" refers to an amelioration of at least one measurable physical parameter, not necessarily discernible by the patient. In yet another embodiment, "treatment" or "treating" refers to reducing the progression of a disease or disorder, for example, by reducing the rate of disease progression compared to a reference population having the same disease or decreasing the degree or rate or progression of a sign or symptom in the subject prior to treatment. In yet another embodiment, "treatment" or "treating" refers to delaying the onset of a disease or disorder, e.g., compared to a reference population or other method of determining such a parameter as is known by those in the art.

The phrase "therapeutically effective amount" as used herein means that amount of therapeutic effective agent that is effective for producing a desired therapeutic effect. Accordingly, a therapeutically effective amount treats or prevents a disease or a disorder, ameliorates at least one sign or symptom of the disorder, e.g., lowers a diabetic patient's glucose level. In various embodiments, the disease or disorder is a diabetes.

The term "therapeutic effect" is art-recognized and refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and conditions in an animal or human.

The term "modulation" is art-recognized and refers to up regulation (i.e., activation or stimulation), down regulation (i.e., inhibition or suppression) of a response, or the two in combination or apart.

The terms "systemic administration," "administered systemically," "peripheral administration" and "administered peripherally" are art-recognized and refer to the administration of a composition, therapeutic or other material other than directly into the central nervous system, such that it enters the patient's system and, thus, is subject to metabolism and other like processes, for example, intravenous, subcutaneous, or oral administration.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection.

The term "inraoral route of delivery" applies to products intended to deliver the drug substance within the mouth, e.g. buccal, lingual, or periodontal. (*Guidance for Industry and Review Staff. Nonclinical Safety Evaluation of Reformulated Drug Products and Products Intended for Administration by an Alternate Route. FDA* 2008, *p.* 6).

D. Terms Related to Pharmaceutics

The term "pharmaceutically acceptable counter ion" refers to a pharmaceutically acceptable anion or cation. In various embodiments, the invention comprises a pharmaceutically acceptable counter ion. The pharmaceutically acceptable counter ion is a pharmaceutically acceptable ion. Non-limiting examples include, but are not limited to citrate, matate, acetate, oxalate, chloride, bromide, iodide, nitrate, sulfate, bisulfate, phosphate, acid phosphate, isonicotinate, acetate, lactate, salicylate, tartrate, oleate, tannate, pantothenate, bitartrate, ascorbate, succinate, maleate, gentisinate, fumarate, gluconate, glucaronate, saccharides, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)).

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Therapeutically effective agents included in the present compositions that include an amino moiety may form pharmaceutically acceptable salts with various amino acids, in addition to the acids mentioned above. Therapeutically effective agents included in the present compositions, that are acidic in nature are capable of forming base salts with various pharmacologically acceptable cations. Examples of such salts include alkali metal or alkaline earth metal salts and ammonium salts.

In addition, if the therapeutically effective agents described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

A pharmaceutically acceptable salt can be derived from an acid selected from 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, hydrochloric acid, isethionic, isobutyric acid, lactic acid, lactobionic acid, lauric acid, maleic acid, malic acid, malonic acid, mandelic acid, methanesulfonic acid, mucic, naphthalene-1,5-disulfonic acid, naphthalene-2-sulfonic acid, nicotinic acid, nitric acid, oleic acid, oxalic acid, palmitic acid, pamoic acid, pantothenic, phosphoric acid, proprionic acid, pyroglutamic acid, salicylic acid, sebacic acid, stearic acid, succinic acid, sulfuric acid, tartaric acid, thiocyanic acid, toluenesulfonic acid, trifluoroacetic, and undecylenic acid.

The term "bioavailable" is art-recognized and refers to a form of the subject disclosure that allows for it, or a portion of the amount administered, to be absorbed by, incorporated to, or otherwise physiologically available to a subject or patient to whom it is administered.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the formulation and not injurious to the patient.

The term "dissolving time" refers to the average time required for complete dissolving of the sublingually administered tablet.

The term "short dissolving time" is when a tablet dissolves in the mouth in less than 3 minutes.

The term "medium dissolving time" is when the tablet dissolves in the mouth in 3 to 15 minutes.

The term "long dissolving time" is when the tablet dissolves in the mouth in 15 to 45 minutes.

The term "very long dissolving time" is when the tablet dissolves in the mouth in 45 to 180 minutes.

II. Formulation Composition

The present teachings provides formulations that deliver a therapeutically effective amount of one or more therapeutically effective agents by transmucosally permeating the agent through the oral mucosa to treat a disease or disorder and methods of using these formulations. One advantage of the present disclosure is that the therapeutically effective agents avoid degradation by acid catalyzed hydrolysis in the stomach and other degradation throughout the gastrointestinal tract. Another advantage of the present disclosure is that the formulation can systemically deliver agents that have limited permeability through the gastrointestinal tract.

In various embodiments, the disclosure permeates therapeutically active agent through the oral mucosa. In various embodiments, the invention permeates a therapeutically active agent through the buccal mucosa. In a various embodiments, the formulation permeates a therapeutically active agent through the sub-lingual mucosa. The invention may permeate 1, 2, 3, or 4 therapeutically active agents through the buccal or sub-lingual mucosa.

A. Therapeutically Active Agents

The present teachings are useful for a variety of therapeutic agents that are known and may be identified by their effects. In some embodiments, the active agent is selected from a biomolecule, bioactive agent, small molecule, drug, prodrug, drug derivative, protein, peptide, vaccine, adjuvant, imaging agent (e.g., a fluorescent moiety) or polynucleotide. In various embodiments therapeutically active agents form pharmaceutically acceptable salts. In various embodiments therapeutically active agents form complexes with pharmaceutically acceptable counter-ions.

In various embodiments the therapeutically active agent is a peptide. Non-limiting examples of therapeutically active peptides include calcitonins, vasopressins, leuprolide, octreotide, glucagon-like peptides, liraglutide, pramlintide, glatiramer, oxytocin, somatostatin, icatibant, hirudin, corticorelin, angiotensin antagonists, cholecystokinin analogues, ziconotide, bradykinin inhibitors, other peptides derivatives and analogues.

In various embodiments the therapeutically active agent is a protein or protein derivative. Non-limiting examples of proteins include interferons, interleukins, tumor necrosis factors, growth factors In various embodiments, the therapeutically active agent is insulin.

B. Carriers and Counter Ions

Various embodiments are formulated with one or more pharmaceutically acceptable carriers. In various embodiments, the carrier is biocompatible, i.e., it does not typically induce an adverse response when inserted or injected into a subject. The adverse response can include significant inflammation and/or acute rejection of the carrier by the immune system, for instance, via a T-cell response. It will be recognized, of course, that "biocompatibility" is a relative term, and some degree of immune response is to be expected even for carrier that are highly compatible with living tissue. However, as used herein, "biocompatibility" refers to the acute rejection of material by at least a portion of the immune system, i.e., a non-biocompatible material implanted into a subject provokes an immune response in the subject that is severe enough such that the rejection of the material by the immune system cannot be adequately controlled, and often is of a degree such that the material must be removed from the subject.

In various embodiments, the carrier is a liquid mixture of one or more substances. In some embodiments, the liquid mixture is hydrophobic and immiscible with aqueous solutions. In various embodiments the liquid mixture solubilizes therapeutically active agents. In various embodiments the liquid mixture solubilize complexes comprising therapeutically active agents and pharmaceutically acceptable counter ions. In various embodiments the liquid mixture solubilize complexes comprising therapeutically active agents and pharmaceutically acceptable salts. In various embodiments the carrier is immiscible with water. Pharmaceutically acceptable carriers may include but are not limited to binders, fillers, lubricants, diluents, non-effervescent disintegrants, effervescent disintegrants, flavor-modifying agents, sweeteners, dispersants, coloring agents, taste masking agents, release-controlling polymers and combinations thereof.

In various embodiments the carrier has a melting point between about −10° C. and about 70° C., about 0° C. and about 60° C., about 10° C. and about 50° C., about 10° C. and about 40° C., about 10° C. and about 35° C., about 15° C. and about 40° C., about 15° C. and about 35° C., about 20° C. and about 35° C., about 25° C. and about 35° C., about 30° C. and about 35° C., or about 25° C. and about 30° C. In various embodiments the solid material has a melting point of about 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., or 45° C. In various embodiments a solid carrier melts when placed in contact with the wet mucosal surface and becomes a liquid carrier.

In various embodiments the carrier is a eutectic mixture. The eutectic mixture may be made up of 2, 3, 4 or 5 compounds.

In some embodiments the carrier is a mixture of compounds where each component is within about 0.01% to 20.0%, 0.01% to 15.0%, 0.01% to 10.0%, 0.01% to 8.0%, 0.01% to 7.0%, 0.01% to 6.0%, 0.01% to 5.0%, 0.01% to 4.0%, 0.01% to 3.0%, 0.01% to 2.0% or 0.01% to 1.0% (w/w) of the eutectic concentrations. For example, 60% of A and 40% of B would be within 10% if the eutectic mixture comprised 50% of A and 50% of B. As another example, 60% of A, 20% of B and 30% of C would be within 10% if the eutectic mixture comprised 50% of A, 30% of B and 20% of C.

Various embodiments comprise a pharmaceutically counter ion. Not wishing to be limited by theory, when counter ions form complexes with active agents, the agent is less hydrophilic and more soluble in hydrophobic solvents. In some embodiments, counter ion complexes are more hydrophobic than the non-complexed agent. In some embodiments, counter ion complexes increase the ratio of agent in the octanol portion of an octanol water mixture by about 1.25 to about 10, about 10 to about 25, about 25 to about 50, about 50 to about 75, about 75 to about 100, about 100 to about 125, about 125 to about 150, about 150 to about 175, about 175 to about 200, about 200 to about 300, about 300 to about 400, about 400 to about 500, about 500 to about 600, about 600 to about 1000 fold, about 1000 to about 2000 fold, about 2000 to about 5000 fold, about 5000 to about 20000 fold, about 20000 to about 100000 fold.

Non-limiting examples of counter ions are diacylphosphatidylglycerol derivatives such as dimyristoyl-, dioleyl-, dipalmitoyl- and distearoyl phosphatidylglycerols, alpha-d-Tocopheryl succinate, sodium dioctylsulfosuccinate, mono- and disubstituted cetylphosphates, cholates, deoxycholates, ammonium glycyrrhizinate, cholesteryl hemisuccinate and cholesteryl sulfate.

C. Penetration Enhancers

Various embodiments comprise one or more penetration enhancers. Penetration enhancers facilitate transcellular and/or paracellular permeation of drugs through the oral mucosa. Not wishing to be held by theory, suggested mechanisms for penetration enhancers include reducing the viscosity and/or elasticity of the mucus layer, increasing the fluidity of the lipid bilayer membranes, or altering tight junctions across epithelial cell layers. Unfortunately, many penetration enhancers are toxic. Additionally, many penetration enhancers must be used in high concentrations, such as greater than 5% (w/w) of the formulation to effectively enhance permeation, which may damage the epithelial cells.

Various embodiments of the invention comprise 1, 2, 3 or 4 penetration enhancers. In some embodiments, a penetration enhancer comprise a mixture of compounds. Nonlimiting examples of penetration enhancers include: polar solvents such as liquid polyethylene glycols, propylene glycol, dimethylsulfoxide and N-methylpyrrolidone; lipid disturbants such as Azone®, decylmethylsulfoxide; non-ionic surfactants such as polysorbates, poloxamers, alkyl glucosides and other sugar esters; anionic surfactants such as sodium lauryl sulfate and salts of fatty acid; phospholipids such as lecithin, phosphatidylcholines; eutectic mixtures or mixtures where each compound is within 1%, 2%, 3%, 4%, 5%, 6%, 7%, 8%, 9% or 10% of the eutectic mixture; bile acids salts such as sodium cholate, desoxycholate, taurocholate and analogs thereof; terpenes such as menthol, borneol, and eucalyptol; chelators such as ethylenediaminetetraacetic acid and citric acid; lipids such as monoglycerides, diglycerides, triglycerides; glycol esters, and various cyclo dextrines.

In some embodiments, the penetration enhancer is one or more surfactants. In various embodiments the surfactant is polysorbates, poloxamers, alkyl glucosides, other sugar esters, sodium lauryl sulfate (SLS), and salts of fatty acid. In further embodiments, the penetration enhancer is a non-ionic surfactant. In various embodiments the non-ionic surfactant is from group of polysorbates, poloxamers, alkyl glucosides or other sugar esters. In additional embodiments, the penetration enhancer is a non-ionic surfactant in low concentration. Various embodiments of the formulations of these teachings contain about 0% to about 20% (w/w) of one or more surfactants. Various embodiments of the formulations of these teachings contain about 0% to about 20% (w/w) of one or more non-ionic surfactants. In various embodiments, the invention may comprise an amount of one or more surfactants or non-ionic surfactants that is about 0.00%, 0.25%, 0.50%, 0.75%, 1.00%, 1.25%, 1.50%, 1.75%, 2.00%, 2.25%, 2.50%, 2.75%, 3.00%, 3.25%, 3.50%, 3.75%, 4.00%, 4.25%, 4.50%, 4.75%, 5.00%, 5.25%, 5.50%, 5.75%, 6.00%, 6.25%, 6.50%, 6.75%, 7.00%, 7.25%, 7.50%, 7.75%, 8.00%, 8.25%, 8.50%, 8.75%, 9.00%, 9.25%, 9.50%, 9.75%, 10.00%, 10.50%, 11.00%, 11.50%, 12.00%, 12.50%, 13.00%, 13.50%, 14.00%, 14.50%, 15.00%, 15.50%, 16.00%, 16.50%, 17.00%, 17.50%, 18.00%, 18.50%, 19.00%, 19.50%, or 20.00% (w/w).

In various embodiments the penetration enhancer is a mixture of 2 to 5 compounds. Some embodiments comprise 2, 3, 4, or 5 compounds. Nonlimiting examples of penetration enhancers include combinations of menthol, vitamin E succinate, hydrogenated or purified lecithins, thymol, vitamin E succinate, fatty acid mixtures such as combination of lauric and stearic acids or lauric, palmitic acids, cholesterol or oleic acid. In various embodiments the mixture of compounds has a melting point between about −10° C. and about 70° C., about 0° C. and about 60° C., about 10° C. and about 50° C., about 10° C. and about 40° C., about 10° C. and about 35° C., about 15° C. and about 40° C., about 15° C. and about 35° C., about 20° C. and about 35° C., about 25° C. and about 35° C., about 30° C. and about 35° C., or about 25° C. and about 30° C. In various embodiments the mixture of compounds has a melting point of about 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., or 45° C. In various embodiments a mixture of compounds melts when placed a patient's mouth.

In some embodiments the penetration enhancer is a eutectic mixture. In various embodiments the eutectic mixture comprises 2 to 5 compounds. The eutectic mixture may contain 2, 3, 4, or 5 compounds. In other embodiments the penetration enhancer is a mixture of compounds where each component is within about 0.01% to 20.0%, 0.01% to 15.0%, 0.01% to 10.0%, 0.01% to 8.0%, 0.01% to 7.0%, 0.01% to 6.0%, 0.01% to 5.0%, 0.01% to 4.0%, 0.01% to 3.0%, 0.01% to 2.0% or 0.01% to 1.0% (w/w) of the eutectic concentrations. For example, 60% of A and 40% of B would be within 10% if the eutectic mixture comprised 50% of A and 50% of B. As another example, 60% of A, 20% of B and 30% of C would be within 10% if the eutectic mixture comprised 50% of A, 30% of B and 20% of C.

In various embodiments the formulation comprises a penetration enhancer comprising a mixture of compounds in low concentrations. Various embodiments of the formulations of these teachings contain about 0% to about 10% (w/w) a penetration enhancer comprising a mixture of compounds. Various embodiments of the formulations of these teachings contain about 0% to about 10% (w/w) of a penetration enhancer comprising a mixture of compounds. In various embodiments, the invention may comprise an amount a penetration enhancer comprising a mixture of compounds that is about 0.00%, 0.25%, 0.50%, 0.75%, 1.00%, 1.25%, 1.50%, 1.75%, 2.00%, 2.25%, 2.50%, 2.75%, 3.00%, 3.25%, 3.50%, 3.75%, 4.00%, 4.25%, 4.50%, 4.75%, 5.00%, 5.25%, 5.50%, 5.75%, 6.00%, 6.25%, 6.50%, 6.75%, 7.00%, 7.25%, 7.50%, 7.75%, 8.00%, 8.25%, 8.50%, 8.75%, 9.00%, 9.25%, 9.50%, 9.75%, or 10.00% (w/w).

D. Formulation of Particles

In various embodiments therapeutic agents are formulated as particles. In various embodiments, particles increase the permeation of therapeutically active agents through the oral mucosa. Without wishing to be held to theory, a particle may increase the permeation of a therapeutically active agent because the entire particle permeates through the oral mucosa. Alternatively, the high concentration of the active agent within the particle located adjacent to the oral mucosa may create a concentration gradient across the oral mucosa which drives the active agent through the oral mucosa.

In some embodiments, the particle is a microparticle, nanoparticle or picoparticle. In still other embodiments, the particle is an emulsion droplet, liposome, micelle, lipoplex or polyplex. Various embodiment comprise a base component which is at least partially hydrophobic. The hydrophobic nature of the base component helps form the particle in aqueous media. In various embodiments the base component is amphiphillic, i.e., having a hydrophilic portion and a hydrophobic portion, or a relatively hydrophilic portion and a relatively hydrophobic portion. The hydrophobic and/or hydrophilic nature of the various base components helps to form the particle in aqueous media. In some embodiments, the base component comprises one or more lipids, one or more polymers or one or more oils.

The particles may have a substantially spherical or non-spherical configuration (e.g., upon swelling or shrinkage). The particles may include polymer blends. In various embodiments, the base component of the particles comprises a polymer, a small molecule, or a mixture thereof. The base component can be biologically derived. For example, the small molecule can be, for example, a lipid. A "lipid," as used herein, refers to a hydrophobic or amphiphilic small molecule. Without attempting to limit the scope of the present teachings, lipids, because of their amphiphilicity, can form particles, including liposomes and micelles.

In some embodiments, the base component comprises a polymer. For example, the polymer can be a biopolymer. Non-limiting examples include peptides or proteins (i.e., polymers of various amino acids), nucleic acids such as DNA or RNA. In certain embodiments, the polymer is amphiphilic, i.e., having a hydrophilic portion and a hydrophobic portion, or a relatively hydrophilic portion and a relatively hydrophobic portion.

In some embodiments, the base component comprises one or more oils. As used herein, an "oil" may be a solid or a liquid at 23° C., but when in a liquid state the oil is immiscible with water. As used herein, "immiscible" refers to compounds that fail to mix in all proportion to form a homogenous solution. When an oil and water are mixed, the two substances may separate to form two separate homogenous layers, form a plurality of oil-in-water particles, or a combination thereof. In certain embodiments, the oil is amphiphilic, i.e., having a hydrophilic portion and a hydrophobic portion, or a relatively hydrophilic portion and a relatively hydrophobic portion.

In various embodiments, the base component is biocompatible, i.e., it does not typically induce an adverse response when inserted or injected into a subject. The adverse response can include significant inflammation and/or acute rejection of the polymer by the immune system, for instance, via a T-cell response. It will be recognized, of course, that "biocompatibility" is a relative term, and some degree of immune response is to be expected even for polymers that are highly compatible with living tissue. However, as used herein, "biocompatibility" refers to the acute rejection of material by at least a portion of the immune system, i.e., a non-biocompatible material implanted into a subject provokes an immune response in the subject that is severe enough such that the rejection of the material by the immune system cannot be adequately controlled, and often is of a degree such that the material must be removed from the subject.

Non-limiting examples of biocompatible polymers that may be useful in various embodiments of the present disclosure include polydioxanone (PDO), polyhydroxyalkanoate, polyhydroxybutyrate, poly(glycerol sebacate), polyglycolide, polysaccharide, polylactide, polycaprolactone, or copolymers or derivatives including these and/or other polymers. For example, the biocompatible polymer is chitosan or its derivatives thereof.

In various embodiments, the base component comprises biologically active material (e.g., insulin), eutectic mixture components (e.g., L-menthol with tocopheryl succinate, capric and lauric acids; L-menthol and alpha-D-tocopherol acetate or alpha-D-tocopheryl succinate, L-menthol and lecithin), one or more hydrophobic components such as biocompatible oil (e.g., medium chain triglycerides, mono-, di- and triglycerides, vitamin E, essential oils, phospholipids) counter-ion (e.g., alpha-D-tocopheryl succinate, dimyristoyl- or distearoyl phosphatidylglycerol, cholesteryl sulfate, lipoic acid or dioctylsulfosuccinate); one or more surfactants (e.g., polysorbate, tocophersolan, PEG stearate, ethoxylated castor oil, sugar ester, fatty acid polyglyceride, phospholipid).

Non-limiting examples of biocompatible oils that may be useful in various embodiments of the present disclosure include monoglcerides, diglycerides, triglycerides, essential oils, tocopherols, tocotrienols, aliphatic and aromatic esters of fatty acids and organic acid. Some oil embodiments comprise eutectic mixtures. In various embodiments the oil has a melting point between about −10° C. and about 70° C., about 0° C. and about 60° C., about 10° C. and about 50° C., about 10° C. and about 40° C., about 10° C. and about 35° C., about 15° C. and about 40° C., about 15° C. and about 35° C., about 20° C. and about 35° C., about 25° C. and about 35° C., about 30° C. and about 35° C., or about 25° C. and about 30° C. In various embodiments the oil material has a melting point of about 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., or 45° C. In various embodiments a solid carrier melts when placed a patient's mouth and becomes a liquid carrier.

In various embodiments, the formulation of the current teachings comprises an emulsifier. As used herein, an "emulsifier" is a substance that stabilizes the formation of particles. Non-limiting examples of emulsifiers that may be useful in various embodiments of the present disclosure include surfactants.

In various embodiments a formulation of the current teachings comprises a small amount of one or more surfactants. In some embodiments the surfactant is between about 0.10% and about 50%, between about 0.1% and about 45.0%, between about 0.1% and about 30%, between about 0.1% and 25% by weight of the base component. In other embodiments, the surfactant is about 0.10%, 0.50%, 0.75%, 0.10%, 1.25%, 1.50%, 1.75%, 2.0%, 2.25%, 2.50%, 2.75%, 3.00%, 3.25%, 3.50%, 3.75%, 4.00%, 4.25%, 4.50%, 4.75%, 5.0%, 5.25%, 5.50%, 5.75%, 6.00%, 6.25%, 6.50%, 6.75%, 7.00%, 7.25%, 7.50, 7.75%, 8.00%, 8.25%, 8.50%, 8.75%, 9.00%, 9.25%, 10.00%, 11.00%, 12.00%, 13.00%, 14.00%, 15.00%, 16.00%, 17.00%, 18.00%, 19.00%, 20.00%, 22.50%, 25.00%, 27.50%, 30%, 35%, 40% or 50% by weight of the base component.

In various embodiments, particles self-form when a formulation of the present teachings is added to an aqueous media. As used herein, "self-form" refers to formation of a particle without substantial mixing. In various embodiments, the particles form upon mixing the formulation in an aqueous media. For example, mixing may occur in-vivo by chewing, tongue motions or saliva movement.

In various embodiments, the particle comprises one or more therapeutically active agents. Some particle embodiments further comprise complexes formed of therapeutically active agents and counter-ions. Other particle embodiments comprise complexes formed of therapeutically active agents and pharmaceutical acceptable salts. In some embodiments, at least one of the therapeutically active agents is contained within a particle of the present teachings. The term "contained within" may mean "located in a cavity of," "entirely embedded in," or "partially embedded in." For example, at least one of the therapeutically active agents can be located in a cavity formed in a particle of the present teachings or otherwise embedded in a particle of the present teachings. In certain embodiments, at least one of the therapeutically active agents is located in the cavity of a particle. In certain embodiments, at least one of the therapeutically active agents is entirely embedded in a particle. In certain embodiments, at least one of the compounds is partially embedded in a particle.

In various embodiments, a substantial amount of at least one of the therapeutically active agents is contained within particles of the present teachings. In some embodiments, about 90% or greater, about 80% or greater, about 70% or greater, or about 60% or greater of the total amount of at least one of the therapeutically active agents included in a formulation of the present invention is contained within the particles. In certain embodiments, about 80% or greater of the total amount of at least one of the therapeutically active agents included in a formulation of the present invention is contained within the particles. In certain embodiments, about 90% or greater of the total amount of at least one of the therapeutically active agents included in a formulation of the present invention is contained within the particles. In certain embodiments, about 95% or greater of the total amount of at least one of the therapeutically active agents included in a formulation of the present invention is contained within the particles.

In various embodiments, about 50% and greater, about 40% or greater, about 30% or greater, about 20% or greater, or about 10% or greater of the total amount of at least one of the therapeutically active agents included in a formulation of the present teachings is contained within the particles. In some embodiments, about 10% or greater of the total amount of at least one of the therapeutically active agents included in a formulation of the present invention is contained within the particles. In some embodiments, about 20% or greater of the total amount of at least one of the therapeutically active agents included in a formulation is contained within the particles. In some embodiments, about 30% or greater of the total amount of at least one of the therapeutically active agents included in a formulation of the present invention is contained within the particles. In some embodiments, about 40% or greater of the total amount of at least one of the therapeutically active agents included in a formulation of the present invention is contained within the particles. In some embodiments, about 50% or greater of the total amount of at least one of the therapeutically active agents included in a formulation of the present invention is contained within the particles.

In various embodiments 50%, 51%, 52%, 53%, 54%, 55%, 56%, 57%, 59%, 60%, 61%, 62%, 63%, 64%, 65%, 66%, 67%, 68%, 69%, 70%, 71%. 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% of the total amount of at least one of the therapeutically active agents included in a formulation of the present teachings is contained within the particles.

In various embodiments, the ratio of the therapeutically active agents to the base component in a solution prior to formation of a plurality of particles may affect the percent loading of the therapeutically active agents in the particle and/or the mean size of the particle. For example, an increase in the percent weight of the therapeutically active agents to the percent weight of the base component may increase the percent loading of the therapeutically active agents within the particle. However, the percent loading of the compound in the particles formed may or may not be related to the weight percent of the therapeutically active agents provided during formation of the particles.

In some embodiments, the percent weight of at least one therapeutically active agent provided in a mixture comprising the therapeutically active agents and the base component is at least about 1%, at least about 5%, at least about 10%, at least about 20%, at least about 30%, at least about 40%, at least about 50%, at least about 60%, at least about 70%, at least about 80%, at least about 90%, at least about 100% of the base component, or greater. In certain embodiments, the percent weight is between about 1% and about 10%, between about 1% and about 5%, between about 5% and about 90%, between about 5% and about 80%, between about 5% and about 50%, about 5% to about 30%, between about 5% and 30%, between about 50% and about 90%, or any range therein. In particular embodiments, the weight percentage is about 1% to about 30% or about 5 to about 20%. For example, the weight percentage can be about 10%.

Without wishing to be bound by theory, the size of a particle may alter the delivery (e.g., loss of payload, drug efflux, aggregations, delivery to desired location, etc.) of a compound of the present teachings from the particles. The size of the particles used in a delivery system may be selected based on the application.

In various embodiments, a substantial amount of a carrier is contained within particles of the present teachings. In some embodiments, 90% or greater, about 80% or greater, about 70% or greater, or about 60% or greater of the total amount of the carrier included in the a formulation of the present teachings is contained within the particles. In certain embodiments, about 80% or greater of the total amount of the carrier included in a formulation of the present teachings is contained within the particles. In certain embodiments, about 90% or greater of the total amount of the carrier included in a formulation of the present teachings is contained within the particles. In certain embodiments, about 95% or greater of the total amount of the carrier included in a formulation of the present teachings is contained within the particles.

In various embodiments, about 50% and greater, about 40% or greater, about 30% or greater, about 20% or greater, or about 10% or greater of the total amount of the carrier included in a formulation of the present teachings is contained within the particles. In some embodiments, about 10% or greater of the total amount of a carrier included in a formulation of the present teachings is contained within the particles. In some embodiments, about 20% or greater of the total amount of a carrier included in a formulation of the present teachings is contained within the particles. In some embodiments, about 30% or greater of the total amount of a carrier included in a formulation of the present teachings is contained within the particles. In some embodiments, about 40% or greater of the total amount of a carrier included in a formulation of the present teachings is contained within the particles. In some embodiments, about 50% or greater of the total amount of a carrier included in a formulation of the present teachings is contained within the particles.

In various embodiments the particle comprises one or more penetration enhancers. In some embodiments the penetration enhancer is one or more surfactants. In some embodiments, the percent weight of the one or more surfactants provided in a mixture comprising the surfactants and the base component is less than about 1%, less than about 5%, less than 10%, less than about 15%, or less than about 20%. In various embodiments the penetration enhancer is about 0.10%, 0.50%, 0.75%, 0.10%, 1.25%, 1.50%, 1.75%, 2.0%, 2.25%, 2.50%, 2.75%, 3.00%, 3.25%, 3.50%, 3.75%, 4.00%, 4.25%, 4.50%, 4.75%, 5.0%, 5.25%, 5.50%, 5.75%, 6.00%, 6.25%, 6.50%, 6.75%, 7.00%, 7.25%, 7.50, 7.75%, 8.00%, 8.25%, 8.50%, 8.75%, 9.00%, 9.25%, 10.00% by weight of the base component.

In various embodiments, a particle may be a nanoparticle, i.e., the particle has a characteristic dimension of less than about 1 micrometer, where the characteristic dimension of a particle is the diameter of a perfect sphere having the same volume as the particle. The plurality of particles can be characterized by an average diameter (e.g., the average diameter for the plurality of particles). In some embodiments, the diameter of the particles may have a Gaussian-type distribution. In some embodiments, the plurality of particles have an average diameter of less than about 300 nm, less than about 250 nm, less than about 200 nm, less than about 150 nm, less than about 100 nm, less than about 50 nm, less than about 30 nm, less than about 10 nm, less than about 3 nm, or less than about 1 nm. In some embodiments, the particles have an average diameter of at least about 5 nm, at least about 10 nm, at least about 30 nm, at least about 35 nm, at least about 40 nm, at least about 45 nm, at least about 50 nm, at least about 65 nm, at least about 100 nm, at least about 150 nm, or greater. In certain embodiments, the plurality of the particles have an average diameter of about 10 nm, about 25 nm, about 50 nm, about 75, about 100 nm, about 150 nm, about 200 nm, about 250 nm, about 300 nm, about 500 nm, or the like. In some embodiments, the plurality of particles have an average diameter between about 10 nm and about 500 nm, between about 50 nm and about 400 nm, between about 100 nm and about 300 nm, between about 150 nm and about 250 nm, between about 175 nm and about 225 nm, or the like. In some embodiments, the plurality of particles have an average diameter between about 10 nm and about 500 nm, between about 20 nm and about 400 nm, between about 30 nm and about 300 nm, between about 30 nm and about 200 nm, between about 30 nm and about 175 nm, between about 30 nm and about 150 nm, between about 30 nm and about 120 nm, between about 30 nm and about 100 nm, or the like. For example, the average diameter can be between about 50 nm and 80 nm.

In some embodiments, the particle has an average characteristic dimension of less than about 500 nm, 400 nm, 300 nm, 250 nm, 200 nm, 180 nm, 150 nm, 120 nm, 100 nm, 90 nm, 80 nm, 70 nm, 60 nm, 50 nm, 40 nm, 30 nm or 20 nm. In other embodiments, the particle has an average characteristic dimension of 10 nm, 20 nm, 30 nm, 40 nm, 50 nm, 60 nm, 70 nm, 80 nm, 90 nm, 100 nm, 120 nm, 150 nm, 180 nm, 200 nm, 250 nm or 300 nm. In further embodiments, the particle has an average characteristic dimension of 10-500 nm, 10-400 nm, 10-300 nm, 10-250 nm, 10-200 nm, 10-150 nm, 10-100 nm, 10-75 nm, 10-50 nm, 50-500 nm, 50-400 nm, 50-300 nm, 50-200 nm, 50-150 nm, 50-100 nm, 50-75 nm, 100-500 nm, 100-400 nm, 100-300 nm, 100-250 nm, 100-200 nm, 100-150 nm, 150-500 nm, 150-400 nm, 150-300 nm, 150-250 nm, 150-200 nm, 200-500 nm, 200-400 nm, 200-300 nm, 200-250 nm, 200-500 nm, 200-400 nm or 200-300 nm.

Other embodiments, objects, features, and advantages will be set forth in the detailed description of the embodiments that follow and, in part, will be apparent from the description or may be learned by practice of the claimed disclosure. These objects and advantages will be realized and attained by the compositions and methods described and claimed herein. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled. It should be recognized that the embodiments above may additionally comprise fillers, glidants, flavoring agents, lubricants, and preservatives.

E. Methods of Treating Diseases and Conditions

In additional aspects, the disclosure features methods of treating a disorder, e.g., diabetes, hyperglycemia, obesity, metabolic syndrome, or other disorders, in a subject in need thereof, the method comprising intraorally administering to the subject a therapeutically effective amount of an active agent in various pharmaceutical formulations described above.

In some embodiments the formulation is administered as a solid pharmaceutical formulation, e.g., such as tablet, chewable tablet, lozenge, powder, dissolving film or gum. In various embodiments the solid pharmaceutical formulation has a melting point below 37° C., and therefore melts in a patient's mouth to form a liquid formulation. In some embodiments the formulation is administered as a liquid formulation.

In various embodiments the formulation is not miscible with the mouth's aqueous environment. In some embodiments the formulation comprises one or more emulsifiers. In additional embodiments the formulation emulsifies to form particles. In various embodiments, the active agent or counter ion complex and the carrier concentrate inside the particle. In some embodiments, one or more penetration enhancers concentrate inside the particle. In some embodiments the presence of the particle next to the oral mucosa creates an environment ideal for diffusion, as the particle has a higher concentration of the therapeutically active agents or counter ion complexes than the epithelial cells lining the oral mucosa. In various embodiments, penetration enhancers facilitate the permeation of the therapeutically active agents or counter ion complexes through the oral mucosa. In other embodiments, the penetration enhancers facilitate the permeation of the entire particle through the oral mucosa. In various embodiments the particle gradually releases the therapeutically active agents or counter ion complexes. In other embodiments the particle bursts and releases the majority of the therapeutically active agents or counter ion complexes at once.

III. Examples

The following examples are intended to illustrate certain embodiments of the present teachings, but do not exemplify the full scope of the present teachings and therefore should not be construed to limit the scope of the present teachings.

A. Investigation of Eutectic Mixtures

Several eutectic mixtures that are formed from physiologically acceptable components and can be given orally were investigated. Table 1 below includes some non-limiting examples of such eutectic compositions.

TABLE 1

Eutectic mixtures of physiologically acceptable compounds

| Components | Melting Temperature | Eutectic Melting Temperature, Approx. |
|---|---|---|
| dl-Lipoic acid | 60-61° C. | 20-24° C. |
| L-Menthol | 41-43° C. | |
| Thymol | 49-51° C. | <0° C. |
| L-Menthol | 41-43° C. | |
| Lecithin S-100 | 225-238° C. | 34-36° C. |
| L-Menthol | 41-43° C. | |
| d-alpha-Tocopheryl acid succinate | 75-76° C. | 22-24° C. |
| L-Menthol | 41-43° C. | |
| Stearic acid | 68-70° C. | 56-58° C. |
| Urea | 130-133° C. | |
| Stearic acid | 68-70° C. | 55-60° C. |
| Benzoic acid | 118-121° C. | |
| Stearic acid | 68-70° C. | 38-45° C. |
| Chlorobutanol Hemihydrate | 74-76° C. | |
| Ethyl Maltol | 88-92° C. | 22-26° C. |
| Chlorobutanol Hemihydrate | 74-76° C. | |
| Ethyl Maltol | 88-92° C. | 62-65° C. |
| Stearic acid | 68-70° C. | |
| Butylated Hydroxytoluene (BHT) | 90-92° C. | 42-44° C. |
| Stearic acid | 67-69° C. | |
| Butylated Hydroxytoluene (BHT) | 90-92° C. | 57-60° C. |
| d-alpha-Tocopheryl acid succinate | 75-76° C. | |

TABLE 1-continued

Eutectic mixtures of physiologically acceptable compounds

| Components | Melting Temperature | Eutectic Melting Temperature, Approx. |
|---|---|---|
| Glyceryl Monocaprylate (Imwitor® 308) | 30-34° C. | <0° C. |
| Thymol | 49-51° C. | |
| Glyceryl Monocaprylate (Imwitor® 308) | 30-34° C. | 16-19° C. |
| L-Menthol | 42-43° C. | |
| Glyceryl Monocaprylate (Imwitor® 308) | 30-34° C. | 22-24° C. |
| Urea | 130-133° C. | |
| Glyceryl Monocaprylate (Imwitor® 308) | 30-34° C. | 24-26° C. |
| Butylated Hydroxytoluene (BHT) | 90-92° C. | |
| d-alpha-Tocopherol acetate | 26-28° C. | <10° C. |
| L-Menthol | 41-43° C. | |
| Lauric acid | 42-44° C. | 31-34° C. |
| Stearic acid | 67-69° C. | |
| Capric acid | 31-32° C. | 15-18° C. |
| Lauric acid | 42-44° C. | |
| L-Menthol | 41-43° C. | 24-26° C. |
| d-alpha-Tocopheryl acid succinate | 75-76° C. | |
| Lecithin Epicuron™ 200 | 235-238° C. | |

The described eutectic compositions could be prepared by combining the components or slight heating, if necessary, to accelerate amalgamation. Formation of eutectic mixtures in some cases may be accelerated by tritration of components. Some of tested eutectic mixtures liquefy in the mouth due to lower melting points (below 37° C.). The formed eutectic mixture may be incorporated into solid dosage forms, such as compressed tablets, lozenges or buccal films.

B. Insulin Potency

One international unit (IU) of human insulin is equivalent to 0.0347 mg of dry crystalline human insulin (28.8 IU/mg). On the other hand, 1 USP unit of Bovine (beef) insulin is equivalent to 0.0342 mg of pure insulin, 1 USP unit of Pork (swine) insulin is equivalent to 0.0345 mg of pure insulin, and 1 USP unit of Human insulin is equivalent to 0.0347 mg of pure insulin.

Following examples of compressed tablets compositions are presented here for a non-limiting illustration purposes. Uncoated tablets were prepared by standard pharmaceutical methods that are known to any skilled person working in the field (e.g., dry blend, direct compression, compaction, granulation, etc.).

C. Sublingual Tablet Containing Insulin

Example 1

Comparator

Sorbitol 20.0 g (Sorbidex® P, Cerestar, USA, or Neosorb® P 150 DC, Roquette, France) was carefully mixed with 196 mg of crystalline insulin (insulin USP, water content 9.5%, 27.7 units/mg of dry material). An amount of 500 mg of finely powdered PEG-3350 NF was added and mixed thoroughly, and then round concave tablets (207 mg weight, 8 mm diameter) were compressed using single punch tablet press. The hardness of the formed tablets was 10-14 kP and the tablets dissolved in the mouth in 4-7 minutes.

Placebo tablets were prepared in a similar manner but without insulin. The hardnes of the formed tablets (205 mg weight, 8 mm diameter) was 10-13 kP. The tablets dissolved in the mouth in 4-7 minutes. Table 2 shows the composition per tablet (in mg) in the compressed tablets that contain insulin but no eutectic mixtures.

TABLE 2

Compressed tablets with insulin (composition per tablet, mg) containing no eutectic mixtures

| | Ex. 1 | Ex. 2 | Ex. 3 | Ex. 4 | Ex. 5 | Ex. 6 | Ex. 7 |
|---|---|---|---|---|---|---|---|
| Insulin crystalline (human recombinant) | 2 | 2 | 2 | 2 | 2 | 2 | 2 |
| Lecithin (NLT 80% PC) | | 20 | 20 | 20 | 20 | 5 | 5 |
| PEG Stearate | | | 20 | | | 20 | 20 |
| Polyvinyl-pyrrolidone (K-90) | | | | | | 20 | 20 |
| Dimyristoyl phosphatidylglycerol sodium salt | | | | | | | 5 |
| Chitosan low molecular weight | | | | 100 | | | |
| Carbomer (Carbopol® 974P NF) | | | | | 100 | | |
| Glutamic acid | | | | 50 | | | |
| Sweetener | | 0.5 | 0.5 | 0.5 | 0.5 | 1 | 1 |
| Silicon dioxide (glidants) | | 20 | 20 | 10 | 10 | 10 | 10 |
| Microcrystalline Cellulose | | 35 | 35 | 20 | 20 | | |
| PEG 3350 (lubricant) | 5 | 5 | 5 | 5 | 5 | 5 | 5 |
| Sorbitol | 200 | | | | | | |
| Xylitol | | 200 | 200 | 100 | 100 | | |
| Mannitol | | | | | | 150 | 150 |

Example 2

Sublingual Insulin Tablet Containing Phospholipid

Tablets were prepared using Xylitol (Xylidex® DC, Cerestar), microcrystalline cellulose (Vivapur® 102), colloidal silicon dioxide and purified soy lecithin. After combining with crystalline insulin and sucralose the blend was carefully mixed, screened and then blended with PEG-3350 and compressed into round (8 mm) concave tablets (hardness 8-10 kP). The formed tablets dissolved in mouth in 8-10 minutes.

Example 3

A Sublingual Insulin Tablet Containing Soy Lecithin and a Non-Ionic Surfactant

Tablets were prepared as described in Example 2 but contained combination of lecithin and selected non-ionic surfactant.

Example 4

A Sublingual Insulin Tablet Containing Lecithin and a Bioadhesive Polymer

Mannitol (Parteck® M200, Merck), microcrystalline cellulose (Vivapur® 102), low molecular weight chitosan (Sigma-Aldrich, USA) and colloidal silicon dioxide were mixed and combined with lecithin. After the addition of crystalline insulin and a sweetener, the mixture was carefully mixed, screened, blended with glutamic acid and PEG-3350 and compressed into oval (6×16 mm) concave tablets (307 mg by weight, hardness 4-6 kP). The formed tablets dissolved in the mouth in 15-25 minutes.

Example 5

Formulation with Carbopol 974P NF (Lubrizol Corp.) was prepared similarly, but without addition of an amino acid. Mannitol (Parteck® M200, Merck), microcrystalline cellulose (Vivapur® 102), Carbopol 974P NF (Lubrizol Corp.), lecithin, polyvinylpyrrolidone and colloidal silicon dioxide were combined. After the addition of crystalline insulin and a sweetener, the blend was mixed, screened and then round 8 mm tablets (approximate weight 257 mg) were compressed to form tablets with 5-9 kP hardness. The formed tablets dissolved in the mouth in 20-35 minutes.

Example 6

Mannitol (Parteck® M200, Merck) and colloidal silicon dioxide were mixed with lecithin, PEG stearate and polyvinylpyrrolidone. After the addition of crystalline insulin and a sweetener, the mixture was screened and then round 8 mm tablets (approximate weight 213 mg) were compressed to form tablets of hardness 7-10 kP hardness that dissolved in the mouth in 15-20 minutes.

Example 7

Mannitol (Parteck® M200, Merck), colloidal silicon dioxide and lecithin, PEG stearate and polyvinylpyrrolidone were mixed thoroughly. The crystalline insulin was added, followed by sodium salt of hydrophobic counter-ion component (Dimirystoyl phosphatidylglycerol) and a sweetener; further mixed, screened and then oval shaped tablets (approximate weight 218 mg) were compressed to form tablets of 5-9 kP hardness. The formed tablets dissolved in the mouth in 10-18 minutes.

Next set of examples describes formulations containing eutectic mixtures. Tablets of Examples 8-13 were prepared similarly to Example 7; however, components of eutectic mixtures were added to the composition. These formulations are presented in Table 3 below.

TABLE 3

Compressed Tablets with Insulin (Composition per Tablet, mg) Containing Eutectic Mixtures of Lecithin, Menthol and Vitamin E

|  | Ex. 8 | Ex. 9 | Ex. 10 | Ex. 11 | Ex. 12 | Ex. 13 | Ex. 14 |
|---|---|---|---|---|---|---|---|
| Insulin | 2.2 | 2.0 | 2.2 | 2.1 | 2.2 | 2.2 | 2.0 |
| Lecithin (NLT 80% PC) | 5 | 7.5 | 7.5 | 7.5 | 7.5 | 7.5 | 5 |
| PEG Stearate | 20 | 20 | 20 | 20 | 20 | 20 | 10 |
| Polyvinyl-pyrrolidone (K-90) | 15 | 15 |  |  |  |  | 10 |
| Polyvinyl-pyrrolidone (K-30) |  |  | 10 | 10 | 10 | 10 |  |
| Menthol | 1 | 1.2 | 4.8 | 5 | 5 | 5 | 5 |
| D-Alpha-Tocopheryl acid succinate | 0.3 | 0.3 | 1.2 | 1.2 | 1.2 | 1.2 | 1.2 |
| Sodium deoxcholate |  |  |  | 5 |  | 5 | 5 |
| Sodium dioctylsulfosuccinate (docusate) |  |  |  |  | 10 |  |  |
| Dimyristoyl phosphatidylglycerol sodium salt |  |  | 7.5 | 7.5 | 7.5 | 7.5 | 7.5 |
| Ammonium Glycyrrhizinate |  | 10 | 10 | 10 | 10 | 10 | 10 |
| Chitosan lactate (low molecular weight) |  |  |  |  |  | 30 |  |
| Polyox WSR COAG 7 mln |  |  |  |  |  |  | 50 |
| Tartaric acid |  |  |  |  | 2 |  |  |
| Succinic acid |  |  |  |  |  | 2 |  |
| Citric acid |  |  |  |  |  |  | 2.5 |
| Vitamin E acetate |  |  | 2 | 2 | 2 | 2 | 2 |
| Sucralose | 1 | 1 | 1 | 1 | 1 | 1 | 1 |
| Silicon dioxide | 10 | 10 | 10 | 10 | 10 | 10 | 10 |
| PEG 3350 (lubricant) | 5 | 5 | 5 | 5 | 5 | 5 | 5 |
| Mannitol | 100 | 150 |  |  |  |  |  |
| Sorbitol |  |  | 130 | 130 | 130 | 110 | 100 |

Example 8

Components of eutectic mixture (Menthol, Vitamin E succinate and lecithin) were combined with Mannitol (Parteck® M200, Merck), colloidal silicon dioxide, PEG stearate and polyvinylpyrrolidone. The crystalline insulin was added, followed by sweetener and lubricant (PEG-3350); further mixed, screened and then round tablets (approximate weight 160 mg) were compressed to form tablets with hardness of 4-5 kP and that dissolved in the mouth in 4-9 minutes.

Example 9-14

These Examples were prepared in a similar manner as described in Example 8; however, Examples 9-14 have higher content of eutectic components and additionally contain different counter-ions and anionic surfactants (ammonium glycyrrhizinate, sodium deoxycholate, sodium dioctylsulfosuccinate) and bioadhesive polymers. In some formulations Sorbitol was used instead of Xylitol. The formulation of Example 13 additionally contained bioadhesive polymer (Chitosan).

Example 15-30

These Examples demonstrate the possibility of incorporating various eutectic components, counter-ions, surfactants and other ingredients into compressed tablet for intraoral (sublingual or buccal) administration. These formulations are presented in Table 4 below.

TABLE 4

Compressed Tablets with Insulin (Composition per Tablet, mg) Containing Various Combinations of Eutectic Components, Surfactants, Polyols and Counter-Ions

| | Ex. 15 | Ex. 16 | Ex. 16 | Ex. 17 | Ex. 18 | Ex. 19 | Ex. 20 | Ex. 21 | Ex. 22 | Ex. 23 |
|---|---|---|---|---|---|---|---|---|---|---|
| Insulin | 2.1 | 2.1 | 2.1 | 2.1 | 2.2 | 2.1 | 2.2 | 2.2 | 2.1 | 2.1 |
| Lecithin S-100 | 8 | 8 | 5 | | | | | | | |
| PEG stearate | | | 20 | 10 | 10 | | 20 | 10 | | 20 |
| Tocophersolan | | | | | | 10 | | | 10 | |
| Polyvinylpyrrolidone (low molecular weight) | 10 | 10 | 10 | 15 | 15 | 15 | 10 | 10 | 15 | 10 |
| Crospovidone | | | | | | 10 | 10 | 10 | | |
| Menthol | 5 | 3 | | | | | | 5 | 5 | 5 |
| Thymol | | 2 | | | | | | | | |
| BHT | | | | | | | | 2.5 | | |
| Glyceryl monocaprylate | | | | | | | | | 10 | |
| Lipoic acid | | | | | | | | | | 2.5 |
| Ammonium Glycyrrhizinate | | 10 | 10 | | | | | | | 10 |
| Tocopherol acetate | | | | | | 5 | | | | 2 |
| Microcrystalline cellulose | | | | 50 | 50 | 50 | | | 50 | |
| Lauric acid | | | | 5 | | | | | | |
| Capric acid | | | | | 5 | | | | | |
| Stearic acid | | | | 5 | 5 | | 5 | 5 | | |
| Oleic acid | | | | | | 5 | | | | |
| Sucralose | 1 | 1 | 1 | 1 | 1 | 1 | 1 | 1 | 1 | 2 |
| Silicon dioxide | 10 | 10 | 10 | 10 | 10 | 10 | 10 | 10 | 10 | 10 |
| PEG 3350 (lubricant) | 5 | 5 | 5 | 5 | 5 | 5 | 5 | 5 | 5 | 5 |
| Xylitol | | | | | 140 | 140 | | | 120 | 150 |
| Mannitol | 180 | 180 | 150 | 150 | | | 180 | 180 | | |

| | Ex. 24 | Ex. 25 | Ex. 26 | Ex. 27 | Ex. 28 | Ex. 29 | Ex. 30 |
|---|---|---|---|---|---|---|---|
| Insulin | 2 | 2 | 2 | 2 | 4.1 | 4.1 | 4.1 |
| Lecithin | 7.5 | 7.5 | 10 | 5 | 10 | 10 | 12 |
| Zinc oxide USP micronized | | | | | | 10 | |
| PEG Stearate | 10 | 20 | 30 | 10 | 18 | | |
| Polysorbate 60 | | | | | | 18 | 25 |
| Polyvinylpyrrolidone (K-90) | | | | | 8 | | |
| Polyvinylpyrrolidone (K-30) | 5 | 5 | 5 | 5 | | 10 | 10 |
| Crospovidone | 10 | 10 | | 10 | 14 | 14 | 18 |
| L-Menthol | 1.8 | 1.8 | 1.8 | 1.8 | 3 | 3 | 4 |
| Natural flavor (essential oil) | 5 | 8 | 8 | 5 | 8 | 8 | 10 |
| Alpha-D-Tocopheryl acid succinate | 0.75 | 1.2 | 1.2 | 1 | 1 | 1 | 2 |
| Sodium deoxycholate | 8 | 8 | 10 | 8 | 12 | 12 | 12 |
| Sodium dioctylsulfosuccinate | | 2 | | | | | |
| Dimyristoyl phosphatidylglycerol sodium salt | 10 | 10 | 10 | | 12 | | 12 |
| Distearoyl phosphatidylglycerol sodium salt | | | | 10 | | 12 | |
| Sodium bicarbonate | | | 8 | | | | |
| Vitamin E acetate | | 4 | 5 | | | 10 | |
| Glyceryl monocaprylate | | | | | | | 10 |
| Tartaric acid | | | | 2 | | | |
| Succinic acid | | | 12 | | | | |
| Sucralose | 1 | 1 | 1.5 | 1 | 1.5 | 1.5 | 1.8 |
| Silicon dioxide | 15 | 15 | 20 | 15 | 20 | 20 | 25 |
| PEG 3350 | 5 | 5 | 6 | 5 | 6 | 8 | 8 |
| Sorbic acid | | | | | 2 | 2 | 2 |
| Isomalt | | | | | 180 | | |
| Mannitol | | | | | | 180 | |
| Sorbitol | 140 | 125 | 180 | 140 | | | 200 |

D. Determination of Insulin Association with Self-Emulsified Composition

Several self-emulsifying compositions containing eutectic mixture, counter-ions and surfactant were investigated for level of insulin association with the oil droplets of an emulsion, formed after dissolution in simulated saliva (12 mmol of monobasic Potassium phosphate, 40 mmol of Sodium chloride, 1.5 mmol of Calcium chloride). Level of insulin association with the colloidal delivery system was determined in solution of the tablet using centrifugal filter device (Microcon®, Millipore Corporation, USA) with membrane molecular weight cut-off 50,000 Dalton.

A placebo tablet and an insulin containing tablet were dissolved separately in equal amounts of simulated saliva at 37° C. 400 mcl of obtained colloids were transferred to the centrifugal filter device and spinned down for 30 minutes at 4000 g. The concentration of insulin in a clear filtrate was determined using an appropriate analytical method. Solution of insulin in simulated saliva was used as a control.

According to obtained results, insulin association with formed colloidal system (oil droplets of the oil-in-water emulsion) was in the range of 50-95% for different compositions.

Glucose Controlling Experiments

Postprandial glucose monitoring was carried out after standardized liquid breakfast (2×235 mL of Nutri-Total™, containing 34 g sugar, 40 g starch (total carbohydrates 108 g), 19 g total fat, 26 g protein; Energy—710 Cal). Each participant received insulin or placebo tablets 30 minutes before standardized liquid breakfast. Blood samples for C-Peptide and glucose test were taken at 30, 60, 120, 180 and 240 minutes.

Glucose blood concentrations were determined using a calibrated glucose meter (Accu-Chek® Aviva, Roche Diagnostics GmbH, Germany) and appropriate test strips. C-Peptide concentration in blood plasma was determined using an appropriate Human C-Peptide ELISA kit (Millipore, USA) and a spectrophotometric plate reader.

In another set of experiments insulin tablets were administered sublingually 2 hours after breakfast, and glucose level was observed for up to 6 hours (Table 5).

TABLE 5

Comparative Glucose Lowering Efficacy of Different Sublingual Formulations

| Code | Description | Maximal glucose level decrease | Glucose drop below baseline level | Lecithin | Eutectic mixture | Oil phase | Self-emulsification |
|---|---|---|---|---|---|---|---|
| Placebo | Tablet contains no insulin | −14% | −1% | − | − | − | − |
| A | Untereated group baseline | −13% | 0% | | N/A | | |
| B | Tablet with lecithin only | −14% | −1% | + | − | − | − |
| C | Mixed micelles tablet | −16% | −3% | + | − | − | + |
| D | Chitosan glutamate | −12% | 1% | + | − | − | + |
| E | Mixed micelles + counter-ion | −16% | −3% | + | − | − | + |
| F | Carboxylic bioadhesive polymer | −15% | −2% | + | − | − | + |
| G | Chitosan base | −12% | 1% | + | − | − | + |
| H | Neutral bioadhesive polymer (Polyox) | −13% | 0% | + | − | − | + |
| I | EM (Menthol based) | −21% | −8% | + | + | − | + |
| J | EM (Menthol-based) + counter-ion | −22% | −9% | + | + | − | + |
| K | Triple EM (Menthol-based) + counter-ions | −22% | −9% | + | + | + | + |
| L | Triple EM (Menthol-based) + counter-ions + bile salt | −23% | −10% | + | + | + | + |
| M | EM + Chitosan lactate | −12% | 1% | + | + | − | + |
| N | No oil phase (no emulsion) | −11% | 2% | − | + | − | − |
| O | EM (Menthol based), bile salt; polar oil phase | −27% | −14% | + | + | − | + |
| P | EM (Menthol based) + bile salt + sodium docusate | −15% | −2% | + | + | + | + |
| Q | EM (Menthol based), efervescent tab (coarse emulsion) | −19% | −6% | + | + | + | + |
| R | EM (Menthol-thymol), hydrophobic C/I | −19% | −6% | + | + | + | + |
| S | EM (menthol-lipoic acid), Tocophersolan | −15% | −2% | + | + | + | + |

| Code | Carboxyl counter-ion (C/I) | Sulfonate C/I | Bioadhesive polymer | Penetr. enhancer | Tablet dissolving time | Relative glucose lowering efficacy, % |
|---|---|---|---|---|---|---|
| Placebo | − | − | − | − | medium | 8% |
| A | | | N/A | | | 0% |
| B | − | − | − | − | medium | 8% |
| C | − | − | − | − | short | 23% |
| D | − | − | + | − | long | −8% |
| E | + | − | − | − | medium | 23% |
| F | − | − | + | − | long | 15% |
| G | − | − | + | − | very long | −8% |
| H | − | − | − | − | medium | 0% |
| I | + | − | − | − | medium | 62% |

TABLE 5-continued

Comparative Glucose Lowering Efficacy of Different Sublingual Formulations

| | | | | | | |
|---|---|---|---|---|---|---|
| J | + | − | − | − | medium | 69% |
| K | + | − | − | + | medium | 69% |
| L | + | − | − | + | medium | 77% |
| M | + | − | + | + | long | −8% |
| N | + | − | − | + | medium | −15% |
| O | + | − | − | + | medium | 108% |
| P | + | + | − | + | short | 15% |
| Q | + | + | − | + | short | 46% |
| R | + | + | + | − | medium | 46% |
| S | + | + | + | − | medium | 15% |

Abbreviations: EM—eutectic mixture; C/I—counter-ion

Figure 8A:
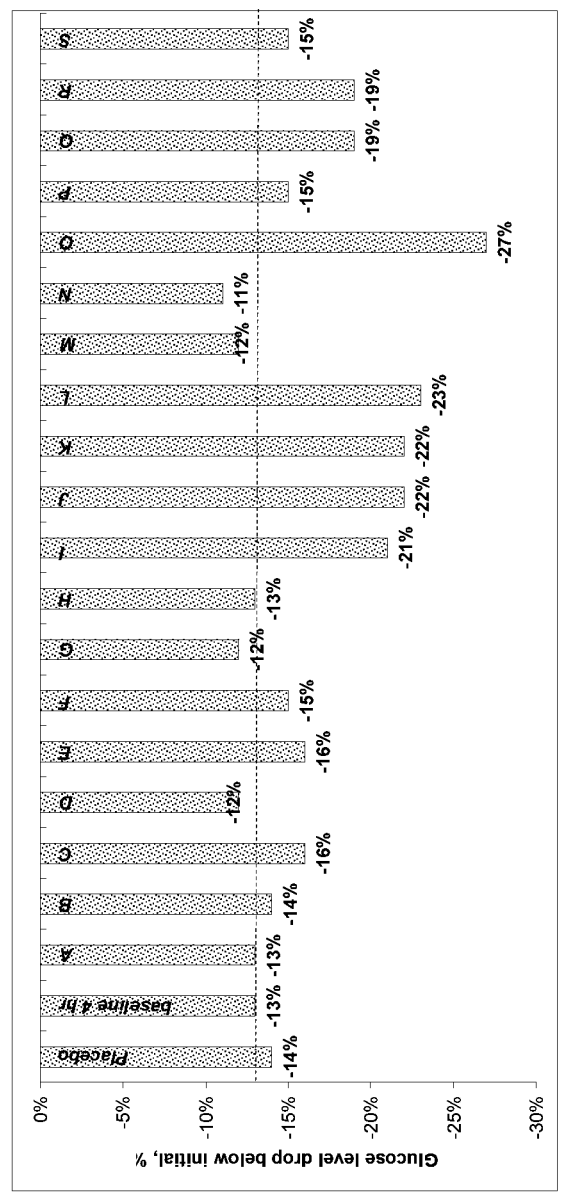
FIGS. 8A and 8B are a graphic presents maximal decrease of glucose in fasting participants (2-6 hours after meals) after sublingual administration of different insulin formulations according to the invention.
Figure 8B:
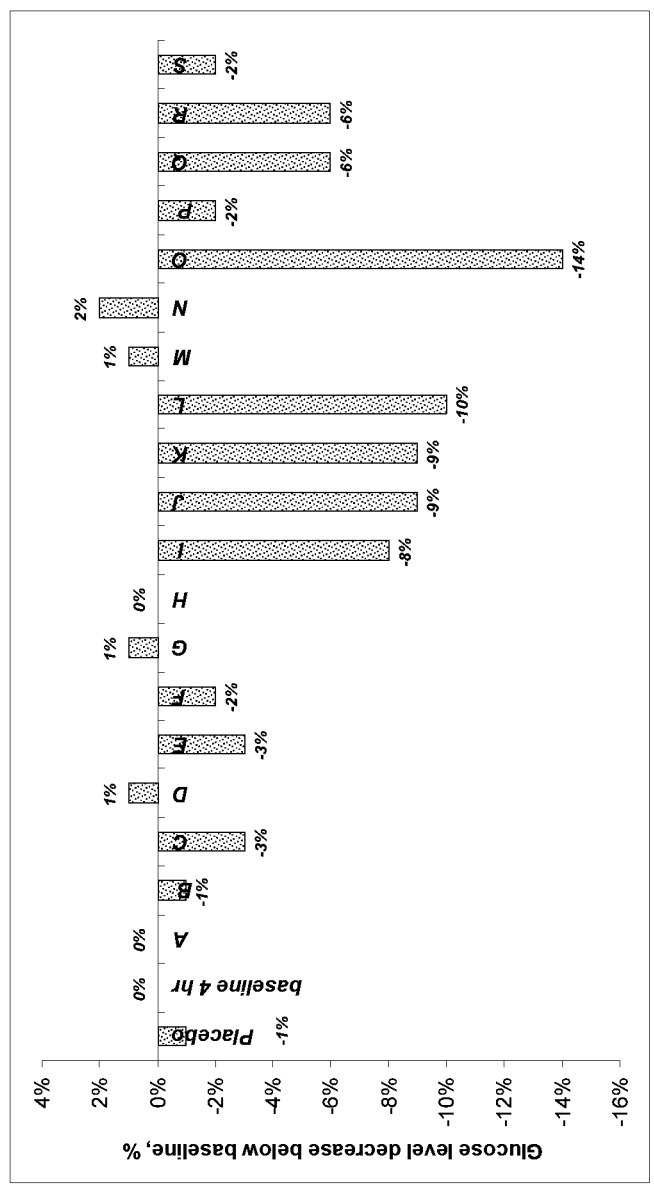
Figure 9:
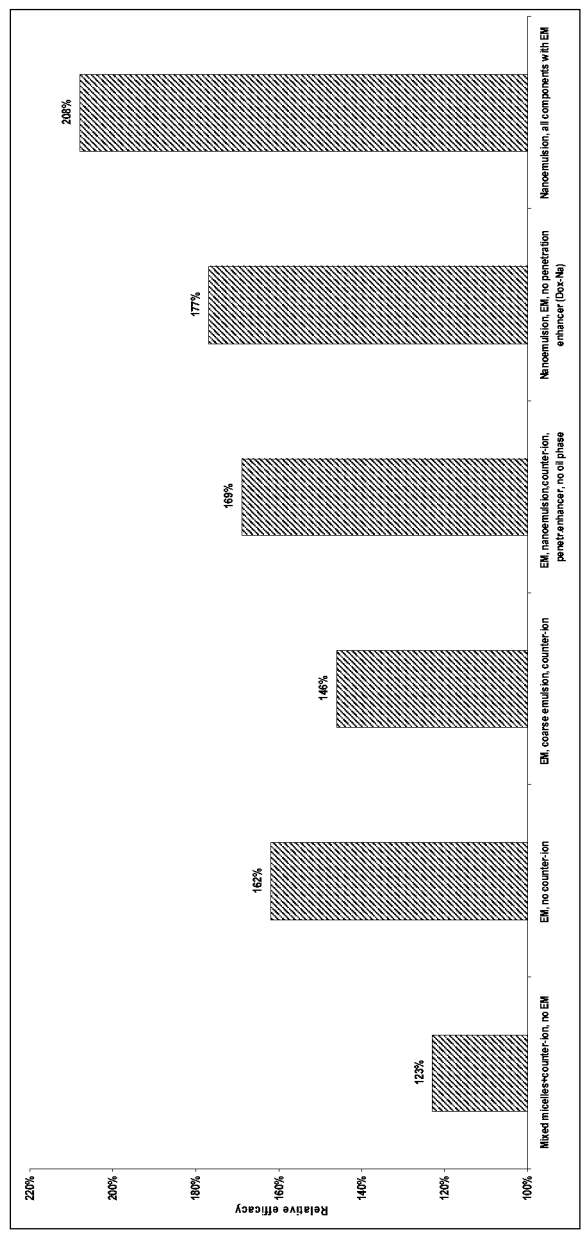
FIG. 9. presents comparative glucose-lowering activity of different formulations at 4 hours in healthy volunteers.

As shown in Table 5, FIG. 8A and FIG. 8B, incorporation of eutectic mixture in the self-emulsifying composition improves insulin transmucosal penetration. The best results were achieved when combination of an eutectic mixture, appropriate surfactant, diacylphosphoglycerol counter-ion and a bile acid was used. Some components, such as bioadhesive polymers, may decrease action of the biologically active peptide, probably, due to extended tablet dissolving in the mouth and lower drug concentration gradient. The use of sulfonated counter ion, such as dioctylsulfosuccinate, in all cases suppressed efficacy of insulin in the tablet. Nevertheless, the use of eutectic mixture in most of the cases visibly improved peptide penetration and glucose lowering action of the dosage form. See FIGS. 1-5 and 9.

Figure 6:
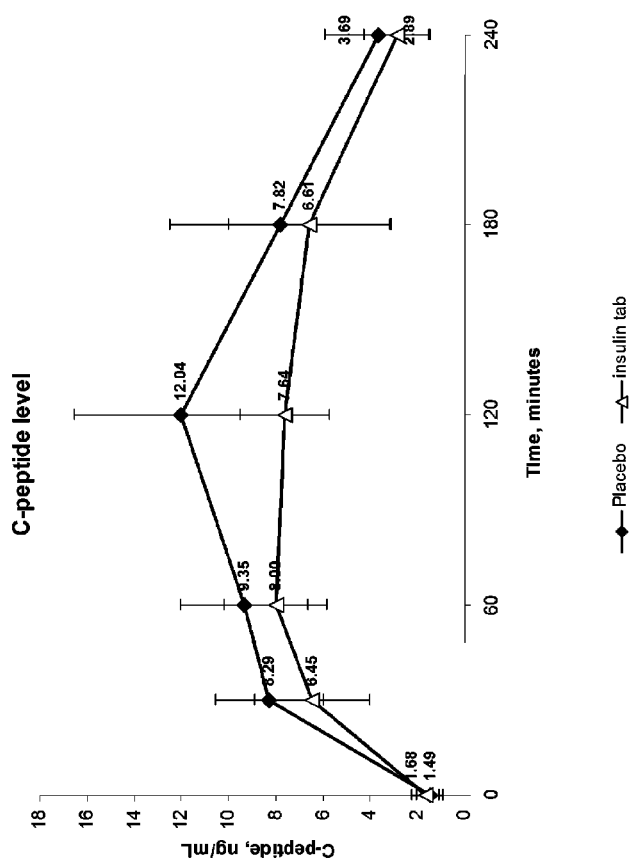
FIG. 6 is a graphic presentation (linear) of C-peptide concentration changes over the time after insulin (100 units) sublingual administration (triangles), compared with C-peptide blood concentrations in placebo treated group (diamonds). Sublingual insulin was delivered at time "0" and visibly decreased C-peptide concentration confirming transmucosal supply of exogenous insulin.
Figure 7:
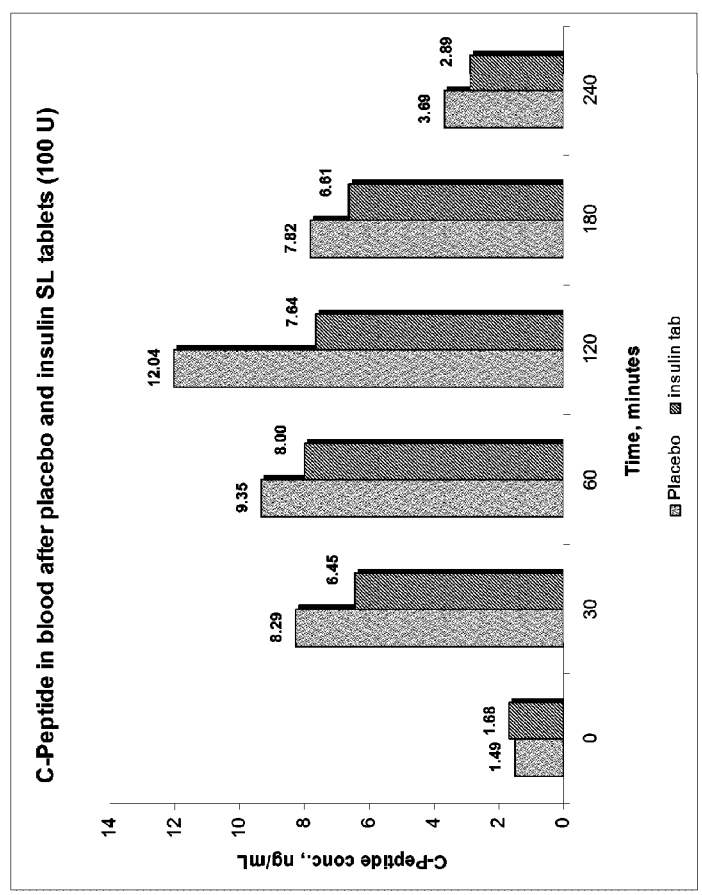
FIG. 7 is a graphic presentation (column) of C-peptide concentration changes over the time after insulin (100 units) sublingual administration, compared with C-peptide blood concentrations in placebo treated group. Sublingual insulin was delivered at time "0" and visibly decreased C-peptide concentration confirming transmucosal supply of exogenous insulin.
Figure 10:
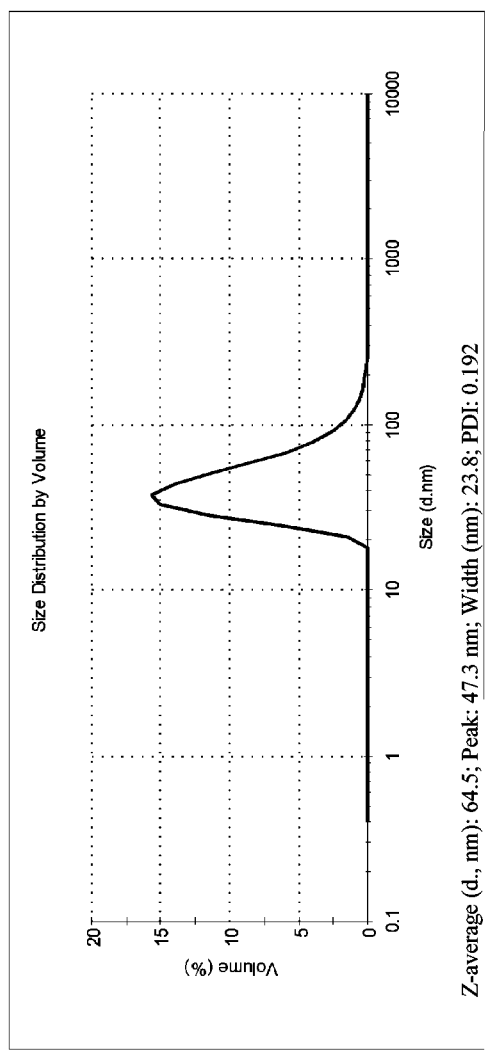
FIG. 10 presents a typical example of particle size distribution of oil-in-water emulsion, formed after self-emulsification of a compressed tablet, containing insulin, hydrophobic eutectic mixture, hydrophobic components for oil phase of the emulsion, hydrophobic counter-ions and surfactants.

The sublingual administration of compressed tablet, containing insulin in a self-emulsifying composition with various components, forming eutectic mixture and other compounds, which form an appropriate oil-in-water emulsion and where insulin could be associated with oil droplets of the emulsion, noticeably decreased the level of blood glucose in human participants either in fasting or in postprandial conditions. The significant decrease of C-peptide concentration in the blood provides a clear evidence of the successful insulin transmucosal delivery (FIG. 6 and FIG. 7). Droplet size of the one of the formed emulsions is shown on FIG. 10.

What is claimed is:

1. A solid pharmaceutical composition, wherein said composition comprises:
    animal or human recombinant insulin in amount of from about 25 to about 600 IU per dosage form; a hydrophobic eutectic mixture preformed from eutectic mixture components and which is liquid at body temperature in amount of from about 1 to about 300 mg per dosage form; a hydrophobic counter-ion in amount of from about 0.5 to about 100 mg per dosage form; at least one oil phase hydrophobic component in amount of from about 0.5 to about 50 mg per dosage form; at least one physiologically acceptable non-ionic or amphiphilic surfactant for self-emulsification in amount of from about 2 to about 200 mg per dosage form; wherein said composition is prepared as an orally dissolving compressed tablet or lozenge for intraoral administration and releases an oil-in-water emulsion upon contact with saliva, and wherein the oil-in-water emulsion has oil droplet size from about 1 nm to about 1000 nm.

2. The solid pharmaceutical composition of claim 1, wherein the eutectic mixture comprises at least two hydrophobic compounds selected from the group consisting of cyclic alcohols, organic acids, phospholipids, monoglycerides, tocopherol derivatives and phenolic compounds.

3. The solid pharmaceutical composition of claim 2, wherein said hydrophobic compound is a tocopherol derivative.

4. The solid pharmaceutical composition of claim 3, wherein said tocopherol derivative is a tocopherol ester.

5. The solid pharmaceutical composition of claim 4, wherein said tocopherol ester is tocopherol acid succinate or tocopherol acetate.

6. The solid pharmaceutical composition of claim 3, comprising tocopheryl acid succinate and L-menthol.

7. The solid pharmaceutical composition of claim 2, wherein said cyclic alcohol in the eutectic mixture is selected from the group consisting of menthol, borneol and thymol.

8. The solid pharmaceutical composition according to claim 7, wherein said cyclic alcohol is L-menthol or racemic menthol.

9. The solid pharmaceutical composition of claim 2, wherein said phenolic compound in eutectic mixture is selected from the group consisting of phenols, cresols and thymol.

10. The solid pharmaceutical composition of claim 9, wherein the eutectic mixture contains thymol.

11. The solid pharmaceutical composition of claim 1, wherein said eutectic mixture comprises combination of at least two aliphatic acids.

12. The solid pharmaceutical composition of claim 11, wherein said eutectic mixture comprises of combination of lauric acid and palmitic or lauric and stearic acid.

13. The solid pharmaceutical composition according to claim 1, wherein said eutectic mixture comprises glyceryl monocaprylate and menthol.

14. The solid pharmaceutical composition of claim 1, wherein said eutectic mixture comprises a phospholipid and a cyclic alcohol.

15. The solid pharmaceutical composition of claim 14, wherein said eutectic mixture comprises a phospholipid and menthol.

16. The solid pharmaceutical composition of claim 15, wherein the phospholipid is lecithin.

17. The solid pharmaceutical composition of claim 1, wherein said composition forms an emulsion after contact with saliva or a water-containing medium.

18. The solid pharmaceutical composition of claim 17, wherein a eutectic mixture is incorporated into a hydrophobic phase of the formed emulsion.

19. The solid pharmaceutical composition of claim 17, wherein insulin is at least partially associated with the hydrophobic phase of the emulsion.

20. The solid pharmaceutical composition of claim 1, further comprising at least one physiologically acceptable hydrophobic component.

21. The solid pharmaceutical composition of claim 20, wherein said physiologically acceptable hydrophobic components is selected from the group consisting of fats, oils, essential oils, mono-, di- and triglycerides, aliphatic, aromatic esters and mixture thereof, and wherein it forms a hydrophobic phase of the emulsion.

22. The solid pharmaceutical composition of claim 1, further comprising at least one physiologically acceptable hydrophobic counter-ion selected from group of organic acids, organic phosphates, negatively charged phospholipids and bile acids.

23. The solid pharmaceutical composition of claim 22, wherein the counter-ion is a negatively charged diacylphosphoglycerol.

24. The solid pharmaceutical composition of claim 1, wherein said solid dosage form is a lozenge, sublingual tablet or orally dissolving tablet.

25. The solid pharmaceutical composition of claim 24, wherein said tablet dissolves in the mouth in a range from about 3 to about 45 minutes.

26. The solid pharmaceutical composition of claim 24, further comprising physiologically acceptable sweeteners, disintegrants, antibacterial preservatives, fillers, flavors, binders, glidants, emulsifiers, colorants and lubricants, wherein the composition is prepared in form of a compressed tablet.

27. The compressed tablet of claim 26, wherein said tablet has hardness not less than 2 kP.

28. The solid pharmaceutical composition of claim 1, wherein said surfactant is selected from the group consisting of physiologically acceptable non-ionic, amphiphilic or anionic surfactants and mixture thereof.

29. The solid pharmaceutical composition of claim 28, containing no lauryl sulfate or other alkylsulfonic acids or salts thereof.

30. The solid pharmaceutical composition of claim 1, wherein said eutectic mixture has a melting point below 60° C.

31. The solid pharmaceutical composition of claim 1, wherein said composition comprises insulin or insulin analog, hydrophobic eutectic mixture, hydrophobic counter-ion, oil phase hydrophobic components and surfactant for self-emulsification, and wherein said composition is prepared as an orally dissolving compressed tablet or lozenge for intraoral administration.

* * * * *